United States Patent
LaVon et al.

(10) Patent No.: US 7,601,145 B2
(45) Date of Patent: *Oct. 13, 2009

(54) DISPOSABLE ABSORBENT ARTICLES HAVING MULTIPLE ABSORBENT CORE COMPONENTS INCLUDING REPLACEABLE COMPONENTS

(75) Inventors: Gary Dean LaVon, Liberty Township, OH (US); Gerald Alfred Young, Miller Township, IN (US); Theodora Beck, Colerain Township, OH (US)

(73) Assignee: The Procter & Gamble Company, Cincinanti, OH (US)

(*) Notice: Subject to any disclaimer, the term of this patent is extended or adjusted under 35 U.S.C. 154(b) by 441 days.

This patent is subject to a terminal disclaimer.

(21) Appl. No.: 10/410,783

(22) Filed: Apr. 9, 2003

(65) Prior Publication Data

US 2004/0030314 A1    Feb. 12, 2004

Related U.S. Application Data

(63) Continuation-in-part of application No. 09/911,108, filed on Jul. 23, 2001, now Pat. No. 6,932,800, which is a continuation-in-part of application No. 09/431,322, filed on Nov. 2, 1999, now abandoned, which is a continuation of application No. 08/825,071, filed on Mar. 27, 1997, now Pat. No. 6,015,935, and a continuation-in-part of application No. 08/828,005, filed on Mar. 27, 1997, now Pat. No. 6,989,005.

(51) Int. Cl.
   *A61F 13/15* (2006.01)

(52) U.S. Cl. .................. 604/385.14; 604/385.01; 604/385.11; 604/385.13; 604/385.19

(58) Field of Classification Search .......... 604/385.14, 604/361, 395, 402, 397, 398, 385.11, 385.19, 604/385.01, 393, 385.13
See application file for complete search history.

(56) References Cited

U.S. PATENT DOCUMENTS 833,849 A    10/1906    Schiff (Continued)

FOREIGN PATENT DOCUMENTS

CN    2073744 U    3/1991

(Continued)

OTHER PUBLICATIONS

U.S. Appl. No. 11/143,691, filed Jun. 2, 2005, All Office Actions and Responses, beginning Jun. 2, 2005.

(Continued)

*Primary Examiner*—Jacqueline F. Stephens
(74) *Attorney, Agent, or Firm*—William E. Gallagher

(57) ABSTRACT

A disposable absorbent article adapted to be worn about a lower torso of a human body and having a chassis, a non-removable absorbent core component disposed in a crotch region of the chassis, and one or more replaceable absorbent core component or components disposed in capillary liquid communication with the non-removable absorbent core component. The replaceable absorbent core component may be removed and a like component may be substituted in place of the removed component without the removal of the absorbent article from the wearer. The replaceable absorbent core component may be disposed inside an openable chassis pocket, with access for its removal and replacement provided by an aperture in a garment-facing layer, an openable end of an external pocket, or an openable end of an internal pocket formed at an area of a waist end edge where the garment-facing layer and a wearer-facing layer may be separated.

8 Claims, 13 Drawing Sheets

U.S. PATENT DOCUMENTS

| | | | |
|---|---|---|---|
| 1,695,109 A | 12/1928 | Kosloff | |
| 1,893,745 A | 1/1933 | Josias | |
| 2,468,445 A | 4/1949 | Hurst | |
| 2,476,585 A | 7/1949 | Cohen | |
| 2,530,647 A | 11/1950 | Buchler | |
| 2,574,279 A | 11/1951 | Oberle | |
| 2,688,328 A | 9/1954 | Marcus | |
| 2,695,025 A | 11/1954 | Andrews | |
| 2,788,786 A | 4/1957 | Dexter | |
| 2,826,199 A | 3/1958 | Brandon | |
| 2,832,346 A | 4/1958 | Morstad | |
| 2,842,129 A | 7/1958 | Ernstorff | |
| 2,868,205 A | 1/1959 | Epstein | |
| 3,050,063 A | 8/1962 | Margraf | |
| 3,162,196 A | 12/1964 | Salk | |
| RE26,151 E | 1/1967 | Duncan et al. | |
| RE26,152 E | 1/1967 | Andren | |
| 3,306,293 A | 2/1967 | Marder et al. | |
| 3,556,932 A | 1/1971 | Coscia et al. | |
| 3,595,235 A | 7/1971 | Jespersen | |
| 3,658,064 A | 4/1972 | Pociluyko | |
| 3,661,875 A | 5/1972 | Sieja | |
| 3,771,524 A | 11/1973 | Ralph | |
| 3,848,594 A | 11/1974 | Buell | |
| 3,860,003 A | 1/1975 | Buell | |
| 3,886,941 A | 6/1975 | Duane et al. | |
| 3,911,173 A | 10/1975 | Sprague, Jr. | |
| 3,918,433 A * | 11/1975 | Fuisz | 600/573 |
| 3,926,189 A | 12/1975 | Taylor | |
| 4,019,517 A | 4/1977 | Glassman | |
| 4,022,210 A | 5/1977 | Glassman | |
| 4,062,817 A | 12/1977 | Westerman | |
| 4,072,150 A * | 2/1978 | Glassman | 604/389 |
| 4,076,663 A | 2/1978 | Masuda et al. | |
| 4,081,301 A | 3/1978 | Buell | |
| 4,093,776 A | 6/1978 | Aoki et al. | |
| 4,257,418 A | 3/1981 | Hessner | |
| 4,260,443 A | 4/1981 | Lindsay et al. | |
| 4,265,245 A | 5/1981 | Glassman | |
| 4,326,302 A | 4/1982 | Lowe et al. | |
| 4,467,012 A | 8/1984 | Pedersen et al. | |
| 4,496,360 A | 1/1985 | Joffe et al. | |
| 4,515,595 A | 5/1985 | Kievit et al. | |
| 4,560,381 A | 12/1985 | Southwell | |
| 4,573,986 A | 3/1986 | Minetola et al. | |
| 4,578,073 A | 3/1986 | Dysart et al. | |
| 4,597,760 A | 7/1986 | Buell | |
| 4,597,761 A | 7/1986 | Buell | |
| 4,605,403 A * | 8/1986 | Tucker | 604/385.13 |
| 4,610,678 A | 9/1986 | Weisman et al. | |
| 4,615,695 A | 10/1986 | Cooper | |
| 4,625,001 A | 11/1986 | Tsubakimoto et al. | |
| 4,654,039 A | 3/1987 | Brandt et al. | |
| 4,666,983 A | 5/1987 | Tsubakimoto et al. | |
| 4,695,278 A | 9/1987 | Lawson | |
| 4,699,619 A | 10/1987 | Bernardin | |
| 4,710,188 A | 12/1987 | Runeman | |
| 4,715,918 A | 12/1987 | Lang | |
| 4,734,478 A | 3/1988 | Tsubakimoto et al. | |
| 4,756,709 A | 7/1988 | Stevens | |
| 4,770,656 A | 9/1988 | Proxmire et al. | |
| 4,773,903 A | 9/1988 | Weisman et al. | |
| D298,566 S | 11/1988 | Runeman | |
| 4,785,996 A | 11/1988 | Ziecker et al. | |
| 4,808,178 A | 2/1989 | Aziz et al. | |
| 4,816,025 A | 3/1989 | Foreman | |
| 4,822,453 A | 4/1989 | Dean et al. | |
| 4,826,499 A | 5/1989 | Ahr | |
| 4,834,736 A | 5/1989 | Boland et al. | |
| 4,834,737 A * | 5/1989 | Khan | 604/385.14 |
| 4,834,738 A | 5/1989 | Kielpikowski et al. | |
| 4,842,666 A | 6/1989 | Werenicz | |
| 4,851,069 A | 7/1989 | Packard et al. | |
| 4,872,871 A | 10/1989 | Proxmire et al. | |
| 4,888,093 A | 12/1989 | Dean et al. | |
| 4,892,598 A | 1/1990 | Stevens et al. | |
| 4,898,642 A | 2/1990 | Moore et al. | |
| 4,923,454 A | 5/1990 | Seymour et al. | |
| 4,938,756 A | 7/1990 | Salek | |
| 4,950,264 A | 8/1990 | Osborn, III | |
| 4,961,736 A | 10/1990 | McCloud | |
| 4,964,857 A | 10/1990 | Osborn | |
| 4,964,860 A | 10/1990 | Gipson et al. | |
| 4,968,312 A | 11/1990 | Khan | |
| 4,988,344 A | 1/1991 | Reising et al. | |
| 4,988,345 A | 1/1991 | Reising | |
| 4,994,037 A | 2/1991 | Bernardin | |
| 5,009,650 A | 4/1991 | Bernardin | |
| 5,009,653 A | 4/1991 | Osborn, III | |
| 5,019,068 A * | 5/1991 | Perez et al. | 604/386 |
| 5,061,259 A | 10/1991 | Goldman et al. | |
| 5,069,672 A | 12/1991 | Wippler et al. | |
| 5,098,423 A | 3/1992 | Pieniak et al. | |
| 5,102,597 A | 4/1992 | Roe et al. | |
| 5,108,385 A | 4/1992 | Snyder | |
| 5,128,082 A | 7/1992 | Makoui | |
| 5,137,537 A | 8/1992 | Herron et al. | |
| 5,141,505 A * | 8/1992 | Barrett | 604/385.13 |
| 5,147,345 A | 9/1992 | Young et al. | |
| 5,149,335 A | 9/1992 | Kellenberger et al. | |
| 5,167,655 A | 12/1992 | McCoy | |
| 5,176,668 A | 1/1993 | Bernardin | |
| 5,181,915 A | 1/1993 | Smith | |
| 5,188,624 A | 2/1993 | Young, Sr. et al. | |
| 5,207,662 A | 5/1993 | James | |
| 5,207,663 A | 5/1993 | McQueen | |
| 5,217,445 A | 6/1993 | Young et al. | |
| 5,236,428 A | 8/1993 | Zajaczkowski | |
| 5,260,345 A | 11/1993 | DesMarais et al. | |
| 5,268,224 A | 12/1993 | DesMarais et al. | |
| 5,318,554 A | 6/1994 | Young et al. | |
| 5,324,561 A | 6/1994 | Rezai et al. | |
| 5,325,543 A | 7/1994 | Allen | |
| 5,358,500 A | 10/1994 | LaVon et al. | |
| 5,360,419 A | 11/1994 | Chen et al. | |
| 5,360,422 A | 11/1994 | Brownlee et al. | |
| 5,383,867 A | 1/1995 | Klinger | |
| 5,387,207 A | 2/1995 | Dyer et al. | |
| 5,401,266 A | 3/1995 | Runeman et al. | |
| 5,405,342 A | 4/1995 | Roessler et al. | |
| 5,409,476 A | 4/1995 | Coates | |
| 5,458,591 A | 10/1995 | Roessler et al. | |
| 5,476,457 A | 12/1995 | Roessler et al. | |
| 5,486,168 A | 1/1996 | Runeman et al. | |
| 5,531,728 A | 7/1996 | Lash | |
| 5,549,589 A | 8/1996 | Horney et al. | |
| 5,550,167 A | 8/1996 | DesMarais | |
| 5,556,393 A | 9/1996 | Rönnberg | |
| 5,562,646 A | 10/1996 | Goldman et al. | |
| 5,563,179 A | 10/1996 | Stone et al. | |
| 5,569,229 A | 10/1996 | Rogers | |
| 5,599,335 A | 2/1997 | Goldman et al. | |
| 5,613,959 A | 3/1997 | Roessler et al. | |
| 5,636,387 A | 6/1997 | Lundy | |
| 5,650,222 A | 7/1997 | DesMarais et al. | |
| 5,667,503 A * | 9/1997 | Roe et al. | 604/385.19 |
| 5,778,110 A * | 7/1998 | Furuya | 383/35 |
| 5,800,416 A | 9/1998 | Seger et al. | |
| 5,817,081 A | 10/1998 | LaVon et al. | |
| 5,827,253 A | 10/1998 | Young et al. | |
| 5,843,055 A | 12/1998 | Seger | |
| 5,843,065 A * | 12/1998 | Wyant | 604/385.09 |
| 5,906,602 A | 5/1999 | Weber et al. | |
| 5,941,863 A | 8/1999 | Guidotti et al. | |

| | | | |
|---|---|---|---|
| 6,015,935 A | 1/2000 | LaVon et al. | |
| 6,083,210 A | 7/2000 | Young et al. | |
| 6,229,061 B1 | 5/2001 | Dragoo et al. | |
| 6,336,923 B1 | 1/2002 | Fujioka et al. | |
| 6,443,933 B1 * | 9/2002 | Suzuki et al. | 604/385.04 |
| 6,623,466 B1 * | 9/2003 | Richardson | 604/385.19 |
| 6,689,114 B2 * | 2/2004 | Bouchard et al. | 604/385.14 |
| 6,766,817 B2 | 7/2004 | de Silva | |
| 6,793,649 B1 | 9/2004 | Fujioka et al. | |
| 6,918,404 B2 | 7/2005 | de Silva | |
| 6,989,006 B2 | 1/2006 | LaVon et al. | |
| 7,066,586 B2 | 6/2006 | de Silva | |
| 7,175,613 B2 | 2/2007 | Sugiyama et al. | |
| 7,285,255 B2 | 10/2007 | Kadlec et al. | |
| 2002/0013566 A1 | 1/2002 | Chappell et al. | |
| 2002/0058286 A1 | 5/2002 | Chappell et al. | |
| 2002/0091368 A1 | 7/2002 | LaVon et al. | |
| 2002/0112982 A1 | 8/2002 | Stagray et al. | |
| 2002/0143311 A1 * | 10/2002 | Brisebois | 604/385.01 |
| 2002/0143316 A1 | 10/2002 | Sherrod et al. | |
| 2003/0199844 A1 | 10/2003 | LaVon et al. | |
| 2003/0220623 A1 | 11/2003 | Sugiyama et al. | |
| 2004/0024379 A1 | 2/2004 | LaVon et al. | |
| 2004/0039361 A1 | 2/2004 | LaVon et al. | |

FOREIGN PATENT DOCUMENTS

| | | |
|---|---|---|
| EP | 0 319 314 A2 | 6/1989 |
| EP | 0 919 213 A2 | 6/1999 |
| GB | 493819 | 10/1938 |
| GB | 734994 | 8/1955 |
| GB | 1411087 | 10/1975 |
| GB | 2042342 | 9/1980 |
| GB | 2 269 998 | 3/1994 |
| GB | 2295321 | 5/1996 |
| JP | 1993-86314 | 11/1993 |
| JP | 6121812 | 5/1994 |
| WO | WO 89/11843 | 12/1989 |
| WO | WO 91/10413 | 7/1991 |
| WO | WO 91/16871 | 11/1991 |
| WO | WO 9116871 A1 * | 11/1991 |
| WO | WO 92/10984 A1 | 7/1992 |
| WO | WO 9424973 A1 * | 11/1994 |
| WO | WO 95/17870 | 7/1995 |
| WO | WO 01/60300 A1 | 8/2001 |

OTHER PUBLICATIONS

U.S. Appl. No. 10/410,782, filed Apr. 9, 2003, All Office Actions and Responses, Apr. 9, 2003 through Oct. 17, 2007 (now U.S. Patent 7,291,137).

U.S. Appl. No. 10/308,430, filed Dec. 3, 2002, All Office Actions and Responses, beginning Dec. 3, 2002.

U.S. Appl. No. 11/430,367, filed May 9, 2006, All Office Actions and Responses, beginning May 9, 2006.

U.S. Appl. No. 11/430,388, filed May 9, 2006, All Office Actions and Responses, beginning May 9, 2006.

U.S. Appl. No. 11/430,744, filed May 9, 2006, All Office Actions and Responses, beginning May 9, 2006.

U.S. Appl. No. 11/430,569, filed May 9, 2006, All Office Actions and Responses, beginning May 9, 2006.

U.S. Appl. No. 11/445,624, filed Jun. 2, 2006, All Office Actions and Responses, beginning Jun. 2, 2006.

U.S. Appl. No. 11/446,460, filed Jun. 2, 2006, All Office Actions and Responses, beginning Jun. 2, 2006.

U.S. Appl. No. 11/430,746, filed May 9, 2006, All Office Actions and Responses, beginning May 9, 2006.

U.S. Appl. No. 11/636,675, filed Dec. 11, 2006, All Office Actions and Responses, beginning Dec. 11, 2006.

U.S. Appl. No. 11/978,051, filed Oct. 29, 2007, All Office Actions and Responses, beginning Oct. 29, 2007.

* cited by examiner

DISPOSABLE ABSORBENT ARTICLES HAVING MULTIPLE ABSORBENT CORE COMPONENTS INCLUDING REPLACEABLE COMPONENTS

CROSS-REFERENCE TO RELATED APPLICATIONS

This application is a continuation-in-part of U.S. application Ser. No. 09/911,108, filed on Jul. 23, 2001 now U.S. Pat. No. 6,932,800 in the name of LaVon et al., confirmation number 4986, which is a continuation-in-part of application Ser. No. 09/431,322, filed on Nov. 2, 1999, now abandoned, which was a continuation of application Ser. No. 08/825,071, filed on Mar. 27, 1997, now U.S. Pat. No. 6,015,935, and is a continuation-in-part of U.S. application Ser. No. 08/828,005, filed on Mar. 27, 1997 now U.S. Pat. No. 6,989,005 in the name of LaVon et al., confirmation number 4421, all of which are hereby incorporated in their entirety herein by reference.

FIELD OF THE INVENTION

This invention relates to disposable absorbent articles, such as disposable diapers and particularly to disposable absorbent articles having multi-piece absorbent cores in which some absorbent core components are non-removable and other absorbent core components are removable and replaceable.

BACKGROUND OF THE INVENTION

Disposable absorbent articles such as disposable diapers, incontinence pads, training pants, and catamenial napkins generally include an absorbent core for receiving and holding bodily exudates. The absorbent core typically includes a fibrous web, which can be a nonwoven, airlaid web of natural or synthetic fibers, or combinations thereof. Fibrous webs used in such absorbent articles also often include certain absorbent gelling materials usually referred to as "hydrogels", "superabsorbents" or "hydrocolloid" materials to store large quantities of the discharged bodily liquids. These materials absorb through capillary or osmotic forces, or a combination of both.

Many absorbent articles such as catamenial pads, adult incontinent products, and diapers are subject to leakage due to an inability to absorb second and subsequent discharges of liquid even if the first liquid discharge has been effectively absorbed. Leakage due to second and subsequent discharges is especially prevalent during the night, when users commonly experience multiple discharges before the absorbent article is changed. One reason for the inability of many absorbent articles to adequately handle multiple discharges of liquid is the inability of the absorbent core to transport discharged liquid away from the region of discharge once the absorbent capacity of that region has been reached. Thus, the overall performance of the absorbent article is limited by the inability to transport the liquid to the farthest reaches of the absorbent core.

An alternative absorbent material capable of providing capillary liquid transport is open-celled polymeric foam. Appropriately made open-celled polymeric foams provide features of capillary liquid acquisition, transport, and storage required for use in high performance absorbent cores for absorbent articles such as diapers. Shaped or contoured absorbent cores made from such open-celled foam materials having particularly desirable liquid transport characteristics are disclosed in U.S. Pat. No. 5,147,345 issued to Young et al. on Sep. 15, 1992. The Young et al. '345 absorbent core includes both a liquid acquisition/distribution member and a liquid storage/redistribution member. The liquid acquisition/distribution member is positioned within the absorbent article in such a way as to receive or contact aqueous bodily liquid which has been discharged into the absorbent article by the wearer of the article. The liquid storage/redistribution member, in turn, is positioned within the article to be in capillary liquid communication with the liquid acquisition/distribution member.

Absorbent cores providing the desirable absorbent characteristics of the Young et al. '345 patent in an exemplary multi-piece configuration are disclosed in U.S. Pat. No. 5,906,602 issued to Weber et al. on May 25, 1999, which describes shaped absorbent cores having a front panel and a back panel in capillary liquid communication with a center section. The center section includes material generally suitable for liquid acquisition/distribution, while the front and back panels include material generally suitable for liquid storage/redistribution.

Despite the advances in absorbent articles and in liquid handling absorbent core materials, absorbent articles having multiple absorbent core components as well as those having unitary absorbent cores are generally designed for single use wear. Once the storage/redistribution member is saturated with bodily discharges, such as urine, the entire absorbent article is generally discarded and replaced. Often parts of the absorbent article are still usable, and except for being unitary with the absorbent core, these parts could be used further. In addition to the added cost and waste associated with discarding reusable materials, it is often inconvenient to remove and replace the entire absorbent article when absorbent core components are saturated.

Absorbent articles having removable absorbent inserts and thereby being potentially usable for more than a single use are known in the art. For example, U.S. Pat. No. 4,597,761 to Buell, issued Jul. 1, 1986, discloses a disposable absorbent insert for use inside an over-garment such as a conventional reusable diaper, or a disposable diaper. Once the absorbent insert becomes saturated it may be removed and discarded. The absorbent article may then be reused with a fresh absorbent insert. However, because the absorbent insert is removable only from the body side of the article, the absorbent article must be removed from the wearer in order to remove the insert. Therefore, the removal of the absorbent insert is often inconvenient and time consuming.

Accordingly, it would be desirable to provide an absorbent article having a replaceable absorbent core component wherein the absorbent core component can be replaced without having to remove the absorbent article from the wearer.

Additionally, it would be desirable to provide an absorbent article having a replaceable absorbent core component and an apertured garment-facing layer, allowing a saturated component of the absorbent core to be removed through the aperture, thereby exposing an unsaturated component and allowing for prolonged use of the reusable portions of the absorbent article.

Furthermore, it would be desirable to provide an absorbent article having a replaceable absorbent core component disposed between a wearer-facing layer and a garment-facing layer, configured such that access to the replaceable absorbent core component is gained by separating the wearer-facing layer and the garment-facing layer in a predetermined area to form an opening.

SUMMARY OF THE INVENTION

The present invention provides a disposable absorbent article adapted to be worn about a lower torso of a human body, including a chassis forming a waist opening and a pair of leg openings and having longitudinally opposed waist end edges, longitudinally opposed waist regions, and a crotch region longitudinally intermediate of the waist regions, a non-removable absorbent core component disposed in the crotch region, and a replaceable absorbent core component disposed in capillary liquid communication with the non-removable absorbent core component.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

Definitions

Figure 1:
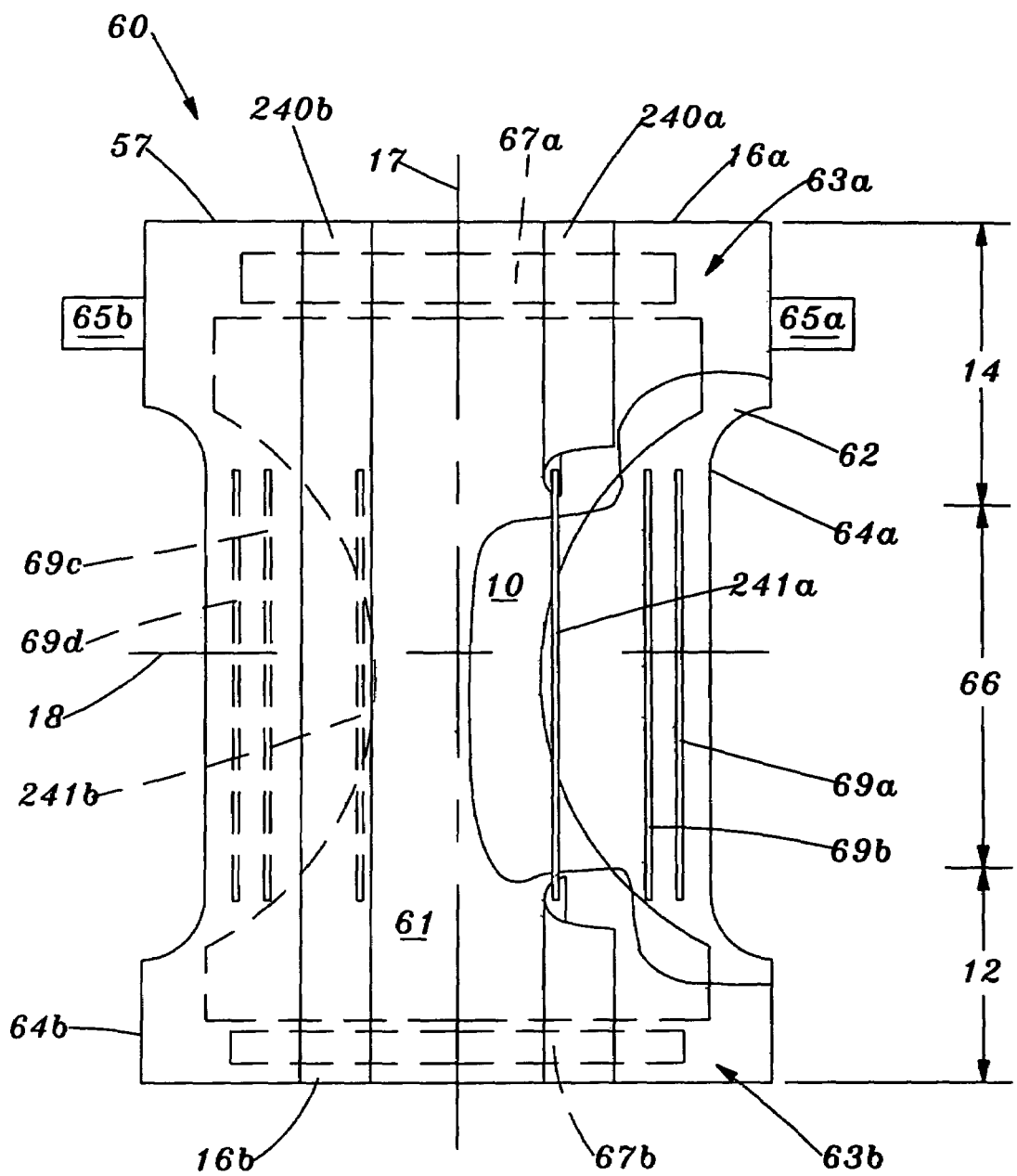
FIG. 1 is a plan view of an exemplary diaper of the present invention in its flat-out, uncontracted state, i.e., with all elastic induced contraction pulled out, with portions of the structure being cut away to more clearly show the construction of the diaper, and with the portion of the diaper that contacts the wearer facing the viewer.

The following definitions of terms may be useful for understanding the disclosure of the present invention.

Absorbent article: A device that absorbs and contains bodily exudates by means of an absorbent core, and, more specifically, a device which is placed against or in proximity to the body of a wearer to absorb and contain the various exudates discharged from the body. An exemplary embodiment of an absorbent article of the present invention is the disposable absorbent article, diaper 60, as shown in the drawing figures. It should be understood, however, that the present invention is also applicable to other absorbent articles such as incontinence briefs, incontinence undergarments, diaper holders and liners, training pants, pull-on diapers, and the like.

Absorbent core: An element of an absorbent article containing a material or a combination of materials suitable for absorbing, distributing, and storing aqueous liquids such as bodily exudates.

Absorbent core component: A structural constituent of an absorbent core, e.g., a piece of an absorbent core, such as one of multiple pieces in a multi-piece absorbent core.

Absorbent layer: A term referring to a discrete, identifiable sheet-like or web-like element of an absorbent core structure which may remain detached and relatively movable with respect to another such element or may be bonded or joined so as to remain permanently associated with another such element. Each absorbent layer may itself include a laminate or combination of several sheets or webs of similar or diverse compositions.

Absorbent member: A functional constituent of an absorbent core, e.g., a liquid acquisition member, a liquid acquisition/distribution member, or a liquid storage/redistribution member formed of a material or materials having particular liquid handling characteristics suitable for the specific function.

Absorbent insert: A device adapted for insertion into an absorbent article and to serve as an absorbent core component when so inserted. A replaceable absorbent core component is an absorbent insert, the latter term being especially descriptive when referring to the device alone.

Chassis: A foundational constituent of an absorbent article upon which the remainder of the structure of the article is built up or overlaid, e.g., in a diaper, the structural elements that give the diaper the form of briefs or short pants when configured for wearing, such as a backsheet, a topsheet, or a combination of a topsheet and a backsheet.

Diaper: An absorbent article generally worn by infants and incontinent persons about the lower torso of the wearer.

Disposable: A term used to describe absorbent articles that are not intended to be laundered or otherwise restored or reused as an absorbent article after use, i.e., that are intended to be discarded after a single use and, preferably, to be recycled, composted or otherwise disposed of in an environmentally compatible manner. Note that, as described in this disclosure, a single use of a chassis and a non-removable core component may correspond to several uses and replacements of replaceable core components.

Capillary liquid communication: The flow of a liquid from one absorbent element to another absorbent element by capillary transport. Also, a term used to describe a structural disposition of absorbent elements in which the flow of a liquid from one of the absorbent elements to the other occurs through capillary transport of the liquid, generally requiring either the direct face-to-face contact of the absorbent elements with each other, the direct face-to-face contact of each of the absorbent elements with a hydrophilic intermediate layer providing capillary conduction of the liquid from one absorbent element to the other, or the protrusion of the fibers of a fibrous absorbent element through a porous and/or permeable intermediate layer into contact with the other absorbent element.

Join, joined, joining: Terms encompassing configurations wherein an element is directly secured to another element by affixing the element directly to the other element, as well as configurations wherein the element is indirectly secured to the other element by affixing the element to an intermediate member or members which in turn is or are affixed to the other element.

Major surface: A term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

Replaceable: A term used to describe a component of an absorbent article that can be replaced, that is, a component that can be removed and for which a like component can be substituted in place of the removed component, e.g., a replaceable absorbent core component or absorbent insert.

Stratum, stratified: Terms referring herein to overlying or superimposed regions within a given layer or structure which have identifiably diverse compositions, densities, or other material properties such that the layer or structure is non-homogeneous through a cross section from one surface to an opposing surface.

Wearer-facing layer: The elements of the chassis that form the inner surface of the absorbent article, such as the topsheet, the leg cuffs, and the side panels, etc., when such elements are present.

Garment-facing layer: The elements of the chassis that form the outer surface of the absorbent article, such as the backsheet, the side panels, the waist fasteners, and the like, when such elements are present.

Overall Description

As described below in detail, the present invention relates to absorbent articles suitable for absorbing and retaining aqueous bodily liquids. These absorbent articles of the present invention generally include a backsheet formed of a substantially liquid impervious material and an absorbent core disposed adjacent to the backsheet. The absorbent core includes at least one removable core component disposed in capillary liquid communication with at least one non-removable core component. The removable core component may be inserted into the absorbent article prior to the application of the absorbent article to the wearer or while the absorbent article is being worn. When the removable core component or a member of it is removed, a replacement absorbent core component or member may be inserted in place of the removed component or member.

In some exemplary embodiments, the absorbent article may include a plurality of absorbent core components, including a front panel and a rear panel in capillary liquid communication with a center section. Each of the absorbent core components may include multiple absorbent layers. Upon saturation with bodily discharges, removable components or absorbent layers of the absorbent core may be removed from the absorbent article. New, unsaturated absorbent core components or absorbent layers may then be positioned in place of the removed saturated core components or absorbent layers.

In some exemplary embodiments, the removable core component is disposed adjacent to the body-facing surface of the backsheet and is accessible through an aperture in the backsheet. In other exemplary embodiments, the removable core component is disposed adjacent to the garment-facing surface of the backsheet and is contained in a pocket formed by a piece of sheet material affixed to the outer surface of the backsheet.

In some exemplary embodiments, the absorbent article includes a liquid pervious topsheet and a substantially liquid impervious backsheet joined to the topsheet about the periphery of the absorbent article. In a predetermined area of the periphery, the topsheet and the backsheet may be separated to form an opening providing access to a removable core component disposed between the topsheet and the backsheet and for the insertion of a replacement core component.

In these exemplary embodiments, the center absorbent core component preferably has suitable liquid acquisition and/or acquisition/distribution characteristics, while the front and rear absorbent core panels or components preferably have suitable storage/redistribution characteristics.

Exemplary Diaper Embodiment

Figure 2:
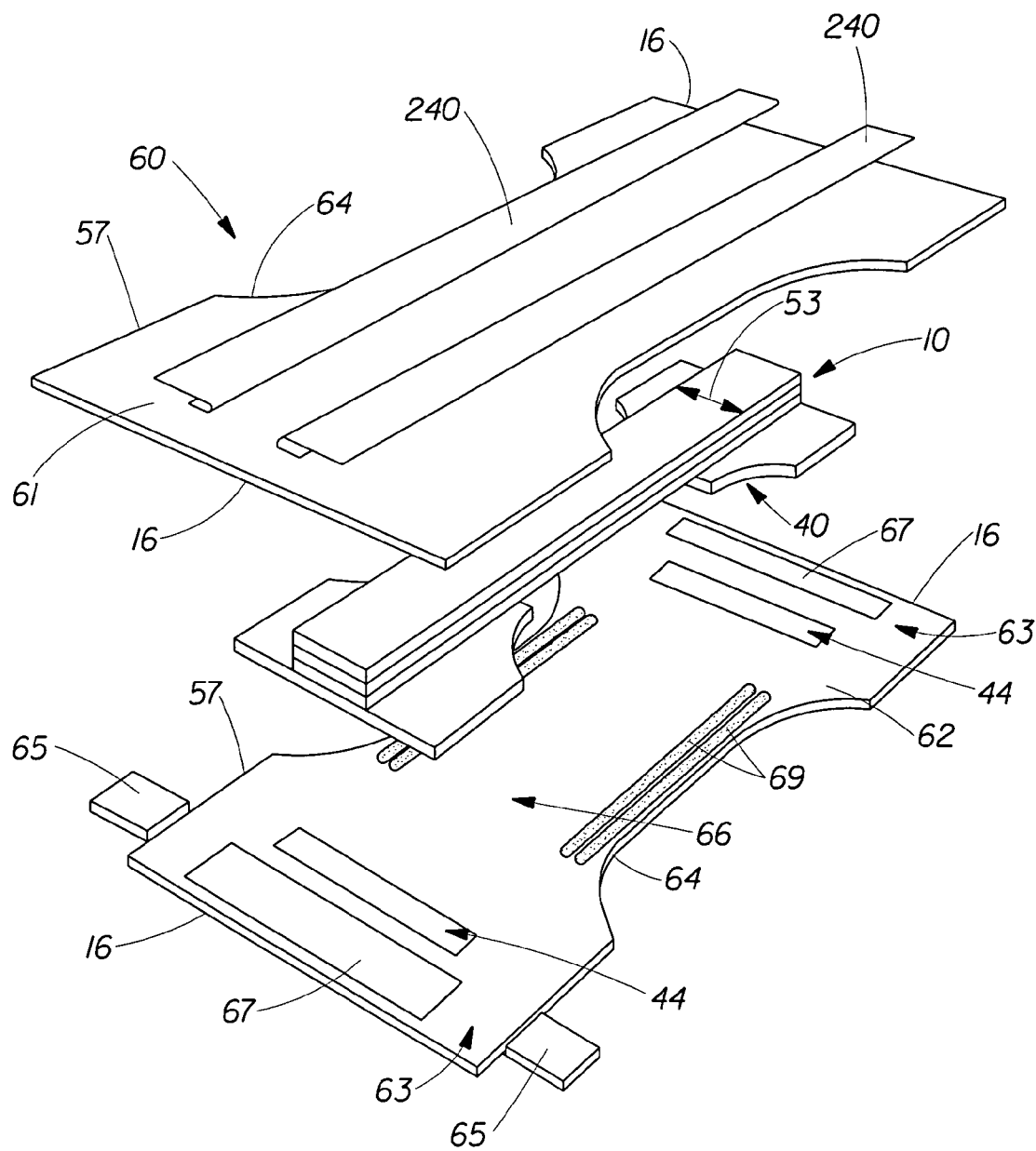
FIG. 2 is an exploded perspective view depicting an exemplary absorbent article, with the portion of the article that contacts the wearer facing upward.

FIG. 1 is a plan view of an exemplary embodiment of an absorbent article of the present invention and shows exemplary diaper 60 in its flat-out, uncontracted state, i.e., with all elastic induced contraction pulled out, with portions of the structure being cut away to more clearly show the construction of the diaper, and with the portion of the diaper which contacts the wearer facing the viewer. FIG. 2 also shows an exemplary diaper 60 in an exploded perspective view, with the portion that contacts the wearer on top. In these exemplary embodiments, the diaper is shown to have a periphery 57 defined by the outer edges of the diaper, with the longitudinal edges being designated 64 and the waist end edges being designated 16. The diaper additionally has a lateral centerline which is designated 18 and a longitudinal centerline which is designated 17. The front waist region 12 and the back waist region 14 extend, respectively, from the waist end edges 16 toward the lateral centerline 18 a distance from about ¼ to about ⅓ the length of the diaper. The waist regions form those portions of the diaper which, when worn, encircle the waist of the wearer. The crotch region 66 is that portion of the diaper between the waist regions, and forms that portion of the diaper which, when worn, is positioned between the legs of the wearer and covers the lower torso of the wearer.

Figure 3:
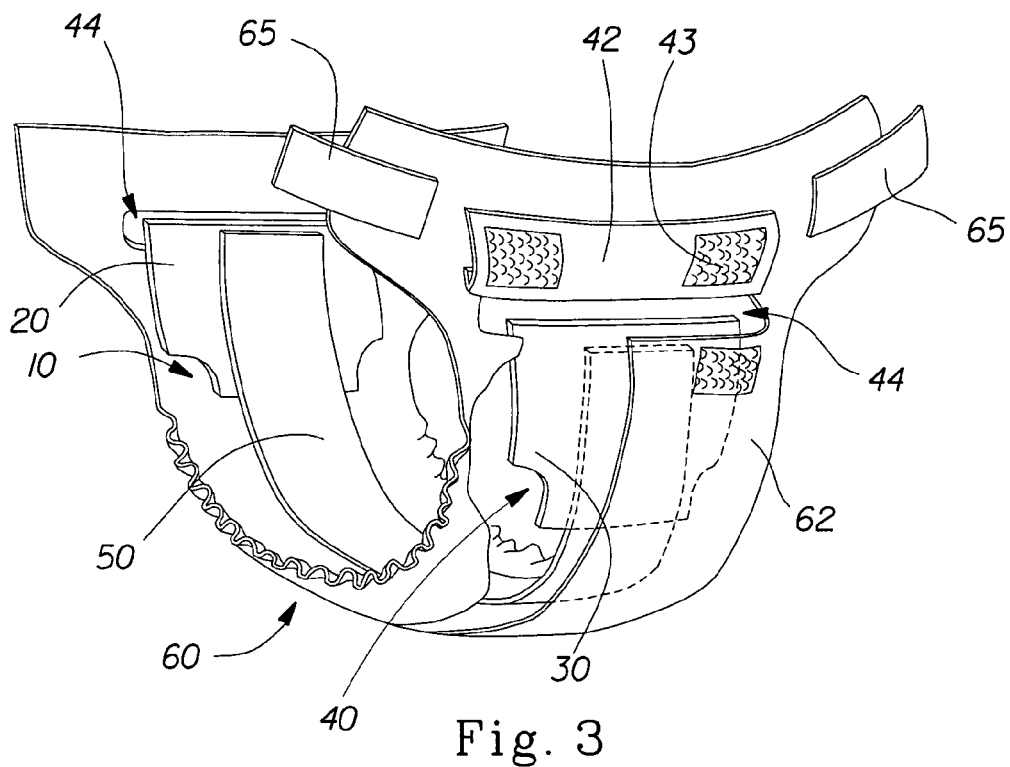
FIG. 3 is a perspective, partially segmented illustration of an exemplary diaper embodiment of an absorbent article according to the present invention.
Figure 4:
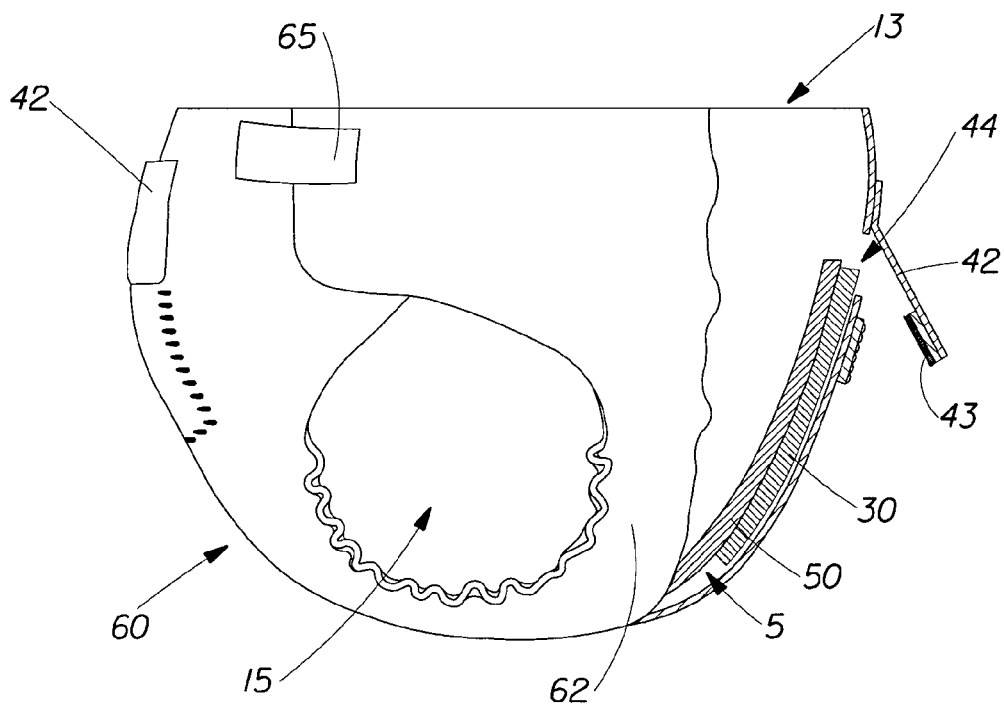
FIG. 4 is a side view, showing in partial cross-section, the exemplary absorbent article of FIG. 3.

Another exemplary disposable diaper 60 embodiment of an absorbent article of the present invention is shown in partially segmented perspective view in FIG. 3 and in a side view, partial cross-section in FIG. 4. The multi-piece absorbent core 10 including multiple absorbent core components, such as the center section 50, the front panel 20, and the back panel 30, is more fully illustrated and described below. The multi-piece absorbent core is also described in the Weber et al. '602 patent.

A multi-piece absorbent core having discrete components provides several benefits. First, the core exhibits desirable aesthetics and fit when used in an absorbent article of the present invention due to the use of discontinuous absorbent layers or panels of absorbent material. For example, the center section may include separate absorbent layers, allowing the center section to bend and buckle somewhat independently from adjacent absorbent layers and the front and rear panels and thereby provide better fit and comfort in the crotch area than is typically achieved with one-piece absorbent cores.

A second advantage provided by a multi-piece absorbent core is the ability to independently vary selected characteristics of the absorbent core components and members. The characteristics that may be varied include the acquisition rates, distribution rates, storage capacities and rates, interfacial liquid transfer rates and efficiencies, thickness, functionality, and the shape or configuration of the absorbent layers or panels. For example, in an exemplary embodiment of an absorbent article of the present invention, three absorbent layers may form the center section, with the absorbent layer closest to the body of the wearer having relatively greater acquisition characteristics than the remaining two outer absorbent layers having relatively greater acquisition/distribution characteristics. In this configuration, bodily discharges such as urine are quickly acquired by the body-side absorbent layer serving as an acquisition member and then desorbed into the adjacent absorbent layers serving as acquisition/distribution members for distribution to the front and back panels, which preferably have greater storage/redistribution characteristics.

A third benefit resulting from the use of a multi-piece absorbent core in an absorbent article of the present invention is the capability of removing and/or replacing components of the absorbent core to regenerate the storage/redistribution capacity of the absorbent core. The provision of access to the removable absorbent core components, for example, to the back panel, allows the removal and/or replacement of those absorbent core components. In this disclosure, all description of the back panels, their removal and replacement, and access to them for their removal and replacement, is generally applicable to the front panels and vice versa, in various exemplary embodiments.

By replacing absorbent core components, particularly absorbent core components that are primarily suited for storage/redistribution, the use of the absorbent article, such as the disposable diaper, may be prolonged while continuing to draw moisture away from the wearer's skin. As storage/redistribution absorbent core members in, e.g., the front panel and the back panel, become saturated, they may become substantially less effective at absorbing moisture from acquisition/distribution members in the center section. Consequently, the center section becomes more saturated, thereby hindering its ability to absorb as much moisture away from the wearer's skin. However, once an absorbent core component such as the back panel is replaced, the absorbent suction of that absorbent core component is regenerated, and it once again becomes capable of absorbing moisture from the acquisition/distribution member of the center section. Therefore, the disposable diaper may be worn longer, and regeneration of the absorbent core may be made without removal of the diaper from the wearer.

It should be understood that the absorbent core described herein may also be useful for other absorbent articles such as incontinent briefs, incontinent pads, training pants, and the like, and that the present invention is not limited to the particular type or configuration of diaper shown in the drawing figures.

In the incorporated references, the entire absorbent core is typically non-removably disposed in the absorbent article. However, as described throughout this disclosure, specific components of the multi-piece absorbent core are removable and replaceable in absorbent articles of the present invention. For instance, the front panel 20 and/or the back panel 30 may be removable and replaceable, while another component, such as the center section 50, may be non-removably disposed in any of the previously known configurations and thereby be made non-removable from the absorbent article. Thus, absorbent articles of the present invention have both non-removable absorbent core components and absorbent core components that are removable and replaceable.

As described in the incorporated references, components of the absorbent core may be made non-removable from the chassis by being secured, attached, affixed, and/or sandwiched to or in the chassis. For example, as described in the Buell '003 patent, an absorbent core component can be rendered immobile by, for example, bonding the backsheet and the absorbent core component together, bonding the absorbent core component to a topsheet and the topsheet to the backsheet, or tightly sandwiching the absorbent core component between a topsheet and the backsheet. Also, as described in the Lawson '278 patent, an absorbent core component may be superimposed on the backsheet and attached thereto by attachment means such as those well known in the art. For example, the absorbent core component may be secured to the backsheet by a uniform continuous layer of adhesive, a patterned layer of adhesive, or an array of separate lines or spots of adhesive. In some exemplary embodiments, an absorbent core component may be affixed in the crotch area of the chassis, as described in the DesMarais et al. '345 patent. Similarly, as described in the Osborn '264 patent, an absorbent core component may be attached over the core's upper or lower major surfaces, respectively, to adjacent members such as the topsheet and the backsheet by any of the means well known in the art, such as by spray-gluing or lines or spots of adhesive. In fact, such attachment may facilitate the integrity and recoverability of the absorbent materials while in use so as to maintain an optimum degree of absorbency.

The Absorbent Article Chassis

As described throughout this disclosure, the liquid absorbent core can be utilized in disposable absorbent products which are capable of absorbing significant quantities of bodily liquids, such as urine, perspiration, menses, and water in bodily wastes. These disposable absorbent articles may be prepared in the form of disposable diapers, adult incontinence briefs, training pants, and the like. Such form-fitting articles will generally include a flexible substrate fashioned into a chassis in the form of briefs or shorts when configured for wearing. A flexible substrate which forms the chassis of such a form-fitting article may include cloth or paper or other kinds of nonwoven substrate or formed films and may be elasticized or otherwise extensible. The chassis is the foundational element upon which the remainder of the structure of the article is built up or overlaid.

Because the designs of the chassis and the absorbent core are interrelated, the absorbent core is included in the following description in order to make the structural relationship between the two clear. A more detailed description of the absorbent core, itself, may be found in the next section of this disclosure.

In the exemplary embodiments shown in FIG. 1 and FIG. 2, the diaper has a substantially liquid impervious backsheet 62. On top of this backsheet is disposed an absorbent core 10 which may include one or more discrete absorbent layers and may include a superabsorbent material in one or more of the absorbent layers. On top of this absorbent core and joined to the backsheet is a fluid pervious topsheet 61. The topsheet is the element of the article that is placed next to the skin of the wearer. Additional structural features such as elastic members and fastening means for securing the diaper in place upon a wearer, such as tape tab fasteners, may also be included, as will be described below.

In these exemplary embodiments, the topsheet and the backsheet are coextensive and have length and width dimensions generally larger than those of the absorbent core. The topsheet is joined with and superimposed on the backsheet, thereby forming the chassis. While the topsheet, the backsheet, and the absorbent core can be assembled in a variety of well known configurations, an exemplary diaper configuration is described generally in the Buell '003 patent. Alternative exemplary configurations for disposable diapers herein are also disclosed in the Aziz et al. '178 patent; the Lawson '278 patent; and the Foreman '025 patent.

The backsheet is typically made of a material substantially impervious to liquids and is preferably manufactured from a thin plastic film, although other flexible liquid impervious materials may also be used. The backsheet prevents the exudates absorbed and contained in the absorbent core from wetting articles, such as bed sheets and undergarments, which contact the diaper. An exemplary backsheet may be made of polyethylene film having a thickness from about 0.013 mm (0.5 mil) to about 0.051 mm (2.0 mils), although other flexible liquid impervious materials can be used. As used herein, the term "flexible" refers to materials which are compliant and which will readily conform to the general shape and contour of the wearer's body. A suitable polyethylene film is manufactured by Monsanto Chemical Corporation and marketed in the trade as Film No. 8020. The backsheet may be embossed and/or matte finished to provide a more clothlike appearance.

At least a portion of the backsheet may be subjected to mechanical stretching to make it elongatable or drawable in order to provide a "zero strain" stretch laminate for, for example, forming elastic side panels.

Further, the backsheet may be "breathable", permitting vapors to escape from the absorbent core while still preventing exudates from passing through the backsheet. It is contemplated that a backsheet that is highly breathable but substantially impervious to liquid may be desirable for certain absorbent articles.

The size of the backsheet is dictated by the size of the absorbent core and the exact diaper design selected. In an exemplary embodiment, the backsheet has a modified hourglass-shape extending beyond the absorbent core a minimum distance of at least about 1.3 centimeters to at least about 2.5 centimeters (about 0.5 to about 1.0 inch) around the entire diaper periphery.

The topsheet is compliant, soft feeling, and non-irritating to the wearer's skin. Further, at least a portion of the topsheet is liquid pervious permitting bodily liquids to readily penetrate through its thickness. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can include natural fibers, e.g., wood or cotton fibers, synthetic fibers, e.g., polymeric fibers such as polyester, polypropylene, or polyethylene fibers, or a combination of natural and synthetic fibers. Preferably, the topsheet is made of a hydrophobic material to isolate the wearer's skin from liquids in the absorbent core. Like the backsheet, at least a portion of the topsheet may be subjected to mechanical stretching to make it elongatable or drawable, in order to provide a "zero strain" stretch laminate for, for example, forming elastic side panels.

A number of manufacturing techniques may be used to manufacture the topsheet. For example, the topsheet can be formed of woven, nonwoven, spunbonded, carded, or like materials. In nonwoven topsheets, the fibers are typically bound together by a thermal binding procedure or by a polymeric binder such as polyacrylate. This sheet is substantially porous and permits a liquid to readily pass therethrough into the underlying absorbent core. The topsheet material will preferably have no affinity for holding aqueous bodily liquids in the area of contact between the topsheet and the wearer's skin.

High loft nonwoven topsheets and apertured formed film topsheets may be used in absorbent articles of the present invention. In some exemplary embodiments, apertured formed films may be preferred for the topsheet because they are pervious to bodily liquids and yet non-absorbent, and they have a reduced tendency to allow liquids to pass through in a direction away from the absorbent core and thereby rewet the wearer's skin. Thus, the surface of the formed film that is in contact with the body remains dry, thereby reducing bodily soiling and creating a more comfortable feel for the wearer. The body-facing surface of the formed film topsheet can be hydrophilic, thereby helping bodily liquids transfer through the topsheet faster and diminishing the likelihood that liquid will flow off the topsheet rather than flowing into and being absorbed by the absorbent core.

The topsheet and the backsheet are joined together in any suitable manner. As used herein, the term "joined" encompasses configurations wherein the topsheet is directly joined to the backsheet by affixing the topsheet directly to the backsheet, and configurations wherein the topsheet is indirectly joined to the backsheet by affixing the topsheet to intermediate members which in turn are affixed to the backsheet. In an exemplary embodiment, the topsheet and the backsheet are affixed directly to each other in the absorbent article's periphery by attachment means (not shown) such as an adhesive or any other attachment means known in the art. For example, a uniform continuous layer of adhesive, a patterned layer of adhesive, or an array of separate lines or spots of adhesive can be used to affix the topsheet to the backsheet. The topsheet may also be adhered to the absorbent core.

Furthermore, it is contemplated that a suitable absorbent core structure without a topsheet could be used to provide desirable results, such as comfort and absorbency, as well as simplicity in manufacturing and material cost savings. For example, the body-side surface of the absorbent core could be made of liquid pervious, soft, compliant, non-irritating materials, thereby making a separate topsheet unnecessary. Such an absorbent core could be used in combination with a backsheet to provide the desired comfort and absorbency in an absorbent article.

Fastening means, such as tape tab fasteners 65, are typically disposed in the waistband region 63 of the diaper for holding the diaper on the wearer. The waistband region is generally considered to be that portion of the diaper extending from the waist end edge of the diaper to about the laterally extending margin of the absorbent core. The tape tab fasteners depicted are representative, only, and the fastening means can be any of those well known in the art, such as the fastening tape disclosed in the Buell '594 patent. These tape tab fasteners or other diaper fastening means are typically applied near the corners of the diaper.

The absorbent article may have an "open" chassis configuration, as shown in FIG. 1, in which the chassis is adapted to be fastened together about the lower torso of a wearer by the fastening means. Alternatively, the absorbent article may have a "closed" chassis configuration, such as that of a pull-on pant-type diaper or training pant, in which the chassis is adapted to be pulled on over the legs and lower torso of the wearer without any additional fastening steps.

Leg elastic members 69 may be disposed adjacent to the periphery of the diaper, preferably along each longitudinal edge 64 to form an elastically contractible leg cuff or side flap, so that the elastic members tend to draw and hold the diaper against the legs of the wearer. The leg elastic members may extend along a portion of the length of the diaper. Alternatively, the leg elastic members can extend the entire length of the diaper, or any other length suitable to provide an elastically contractible line. The length of the leg elastic members is dictated by the diaper design.

A barrier leg cuff 240 including a barrier leg cuff elastic member 241 may be disposed adjacent to each longitudinal edge 64 or between the longitudinal edge and the longitudinal centerline 17 of the diaper. Suitable barrier leg cuff materials and structures are described in the Lawson '278 patent, in the Young et al. '345 patent, in the DesMarais et al. '345 patent, in the Dyer et al., '207 patent, in the Foreman '025 patent, and in the Aziz et al. '178 patent.

Additionally, waist elastic members 67 can be disposed adjacent to either the front, the back, or both of the waistband regions of the diaper to provide a waistband as well as or rather than leg cuffs. While the waistband can comprise a separate element affixed to the body of the disposable diaper, it more often is an extension of other elements of the disposable diaper, such as the backsheet or the topsheet or both the backsheet and the topsheet. Disposable diapers are normally constructed so as to have two waistbands: a front and a rear.

A suitable waistband is disclosed in the Kievit et al. '595 patent. In one exemplary embodiment illustrated in the Kievit et al. '595 patent, elastic waist elements extend across essentially the entire lateral width of the disposable diaper. While this construction may be preferred in some exemplary embodiments, similar waistbands may be useful in designs wherein the elastic waist elements extend across only a portion of the lateral width of the diaper. Preferably, the elastic waist elements extend across a major portion of the lateral width of the disposable diaper.

The elastic members are secured to the diaper in an elastically contractible condition so that in a normally unrestrained configuration, the elastic members effectively contract or gather portions of the diaper. The elastic members can be secured in an elastically contractible condition in at least two ways. For example, the elastic members can be stretched and secured while the diaper is in an uncontracted condition. Alternatively, the diaper can be contracted, for example, by pleating, and the elastic members can be secured and connected to the diaper while the elastic members are in their unrelaxed or unstretched condition. A method and apparatus suitable for manufacturing a disposable diaper having elastically contractible elastic members is described in the Buell '301 patent.

In use, an open chassis version of the diaper is applied to a wearer by positioning one waistband region under the wearer's back, and drawing the remainder of the diaper between the wearer's legs so that the other waistband region is positioned across the front of the wearer. The tape-tab or other fasteners are then secured, preferably to outwardly facing areas of the diaper, as shown in FIG. 4, for example. As can be seen in FIG. 4, the chassis forms a waist opening 13 and leg openings 15 when configured for wearing.

The Absorbent Core

In use, the disposable diapers or other absorbent articles of the present invention tend to more quickly and efficiently distribute and store liquids and to remain dry due to the high absorbent capacity of the absorbent core components. Disposable diapers incorporating the absorbent core components of the present invention can also be thinner and more flexible.

Figure 5:
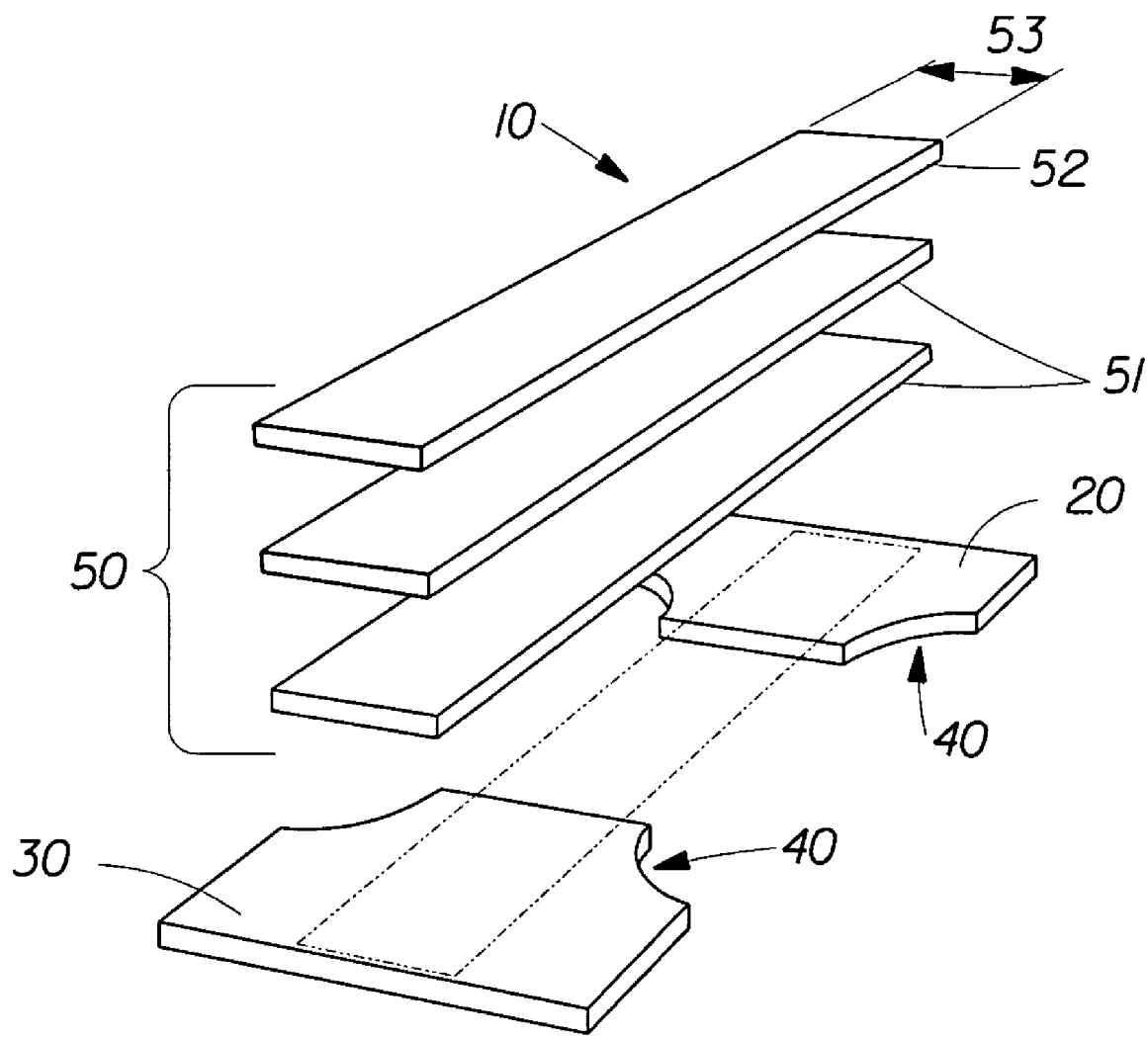
FIG. 5 is an exploded perspective view depicting the relationship between the elements of an exemplary absorbent core of the present invention, with the portion of the core that faces the wearer facing upward.
Figure 6:
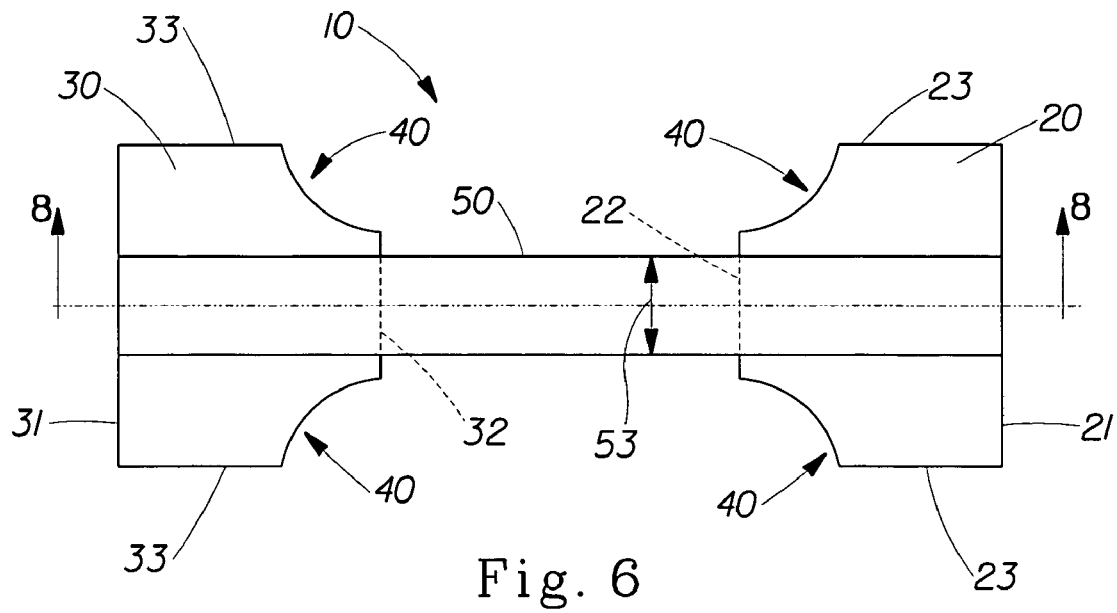
FIG. 6 shows a top plan view of an exemplary absorbent core useful in an absorbent article according to the present invention.

FIG. 5 shows an exploded perspective view depicting the elements of an exemplary embodiment of a shaped absorbent core 10 such as may be used in an absorbent article according to the present invention, for example, in a disposable diaper. FIG. 6 shows a top plan view of such a shaped absorbent core 10.

As depicted in FIG. 5 and FIG. 6, the absorbent core 10 includes a front panel 20 and a back panel 30, both made of absorbent material, preferably material suitable for liquid storage/redistribution. The front panel has an outer front end 21, an inner front end 22, and a pair of sides 23. Similarly, the back panel has an outer back end 31, an inner back end 32, and a pair of sides 33. In this exemplary embodiment, the front and back panels, together with the center section 50, generally form an elongated hourglass shape suitable for use in a disposable diaper or similar absorbent article.

Since the center section 50 and the front panel 20 and the back panel 30 are discrete absorbent core components, the center section 50 may be non-removable, while the front panel 20 or the back panel 30, or both, may be removable from the diaper 60. Thus, when the front panel 20 or the back panel 30 becomes saturated with bodily discharges, such as urine, it can be removed and replaced with a fresh panel for continued use of the absorbent article.

The center section may be generally rectilinear. The term "generally rectilinear" refers to the center section having a generally constant width along its length. In general, however, the center section may have a varying width along its length. The center section may extend from about the outer front end 21 of the front panel, to about the outer back end 31 of the back panel, as shown in FIG. 6. In use, however, the center section need only be in capillary liquid communication with the front and back panels, such as by overlapping in a layered relationship, and may not extend to the outer front end or the outer back end.

In an exemplary embodiment, the width 53 of the center section is suitable for comfortably fitting within the crotch area of the wearer when the absorbent core is incorporated into an absorbent article, such as a disposable diaper. The length of the generally rectilinear center section may be varied to provide a suitable fit for various wearer sizes.

In a generally flat, unfolded state, the front panel and the back panel are disposed such that the inner front end 22 of the front panel is opposed to and spaced from the inner back end 32 of the back panel as shown in FIG. 5 and FIG. 6. The distance between the front and back panels may be varied as necessary. In general, the distance will increase as the crotch length increases with the size of the absorbent article. The front panel generally lies in the front waist region, with the outer front end 21 being generally near the front waist end edge and the inner front end 22 lying in the crotch region. Similarly, the back panel lies in the back waist region, with the outer back end 31 being generally near the back waist end edge and the inner back end 32 lying in the crotch region. In some exemplary embodiments, the back panel 30 is longer than the front panel 20. Such a configuration lends itself to a better fit when the absorbent core is used in a disposable diaper.

As shown in FIG. 2, FIG. 3, FIG. 5, and FIG. 6, the front panel 20 may have cut-out areas 40 at the intersection of the sides 23 and the inner front end 22 and the back panel 30 may have cut-out areas 40 at the intersection of the sides 33 and the inner back end 32. The cut-out areas, or notched portions, join the sides and the inner ends such that the resulting widths of the inner ends 22 and 32 are narrower than those of the outer ends 21 and 31, respectively and, as shown in the figures, approach the width 53 of the center section, which is suitable for comfortably fitting within the crotch area of the wearer when the absorbent core is incorporated into an absorbent article, as stated above. The term "notched" refers to a shape in which, instead of a side and an end meeting generally at a right angle, some amount of material is removed from the corner to produce an additional edge portion joining the side and the end. The additional edge portion of the cut-out areas may be generally straight, but in an exemplary embodiment it is generally arcuate, as depicted in FIG. 6. It is also contemplated that the cut-out areas may have generally straight sides, with the limiting example resulting in a back panel or a front panel being substantially trapezoidal in shape.

Figure 7:
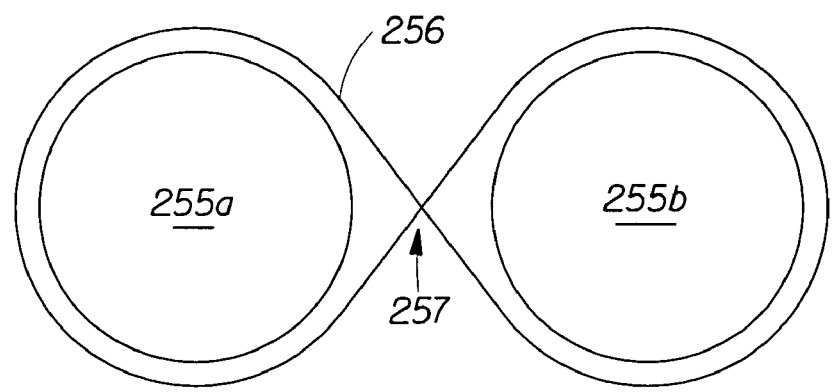
FIG. 7 is a simplified plan view illustrating the method of determining the crotch point of an absorbent article.

A point of reference for the distance that the front panel or the back panel extends from the respective waist end edge is the crotch point of the absorbent article. The "crotch point" of an absorbent article and of the absorbent article's absorbent core is determined by placing the article on a wearer of the physical size for which the absorbent article is designed in a standing position with his or her feet a shoulder width apart and then placing an extensible filament 256 around the legs 255 in a figure eight configuration as shown in FIG. 7. The point in the absorbent article and the absorbent core corresponding to the point of intersection 257 of the filament is considered to be the crotch point of the absorbent article and of the absorbent core. It is understood that the crotch point is determined by placing an absorbent article in the intended manner on a wearer of the correct size for the article and determining where the crossed filament would contact the absorbent article and/or the absorbent core.

Figure 13:
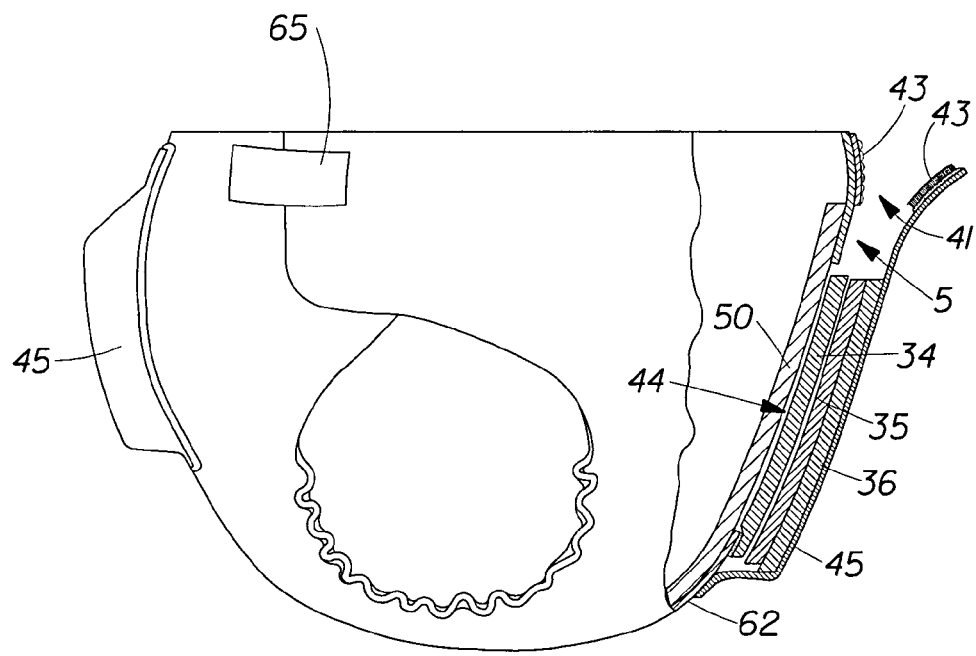
FIG. 13 is a side view, showing in partial cross-section, another alternative exemplary absorbent article.

The center section may include multiple layers of absorbent material, each having individual liquid acquisition, acquisition/distribution or storage/redistribution characteristics, as well as individual shape, width, length and thickness characteristics. The number and placement of absorbent layers of the center section may be varied to achieve desired characteristics such as thinness, softness, flexibility, or beneficial liquid acquisition, distribution, and storage rates. The number of absorbent layers of the front and back panels may also be varied to achieve desired characteristics such as beneficial liquid acquisition and distribution rates, as well as capacity and storage rates, and wearer comfort. For example, in FIG. 3, the absorbent core is shown with the center section 50 and the front and back panels 20 and 30 each having a single absorbent layer. However, the center section has three absorbent layers in the exemplary embodiments shown in FIG. 2 and FIG. 5, with two absorbent layers designated 51 and one absorbent layer designated 52. Also, the back panel is shown in FIG. 13 as a core component made up of back panel absorbent layers 34, 35, and 36.

Figure 8:
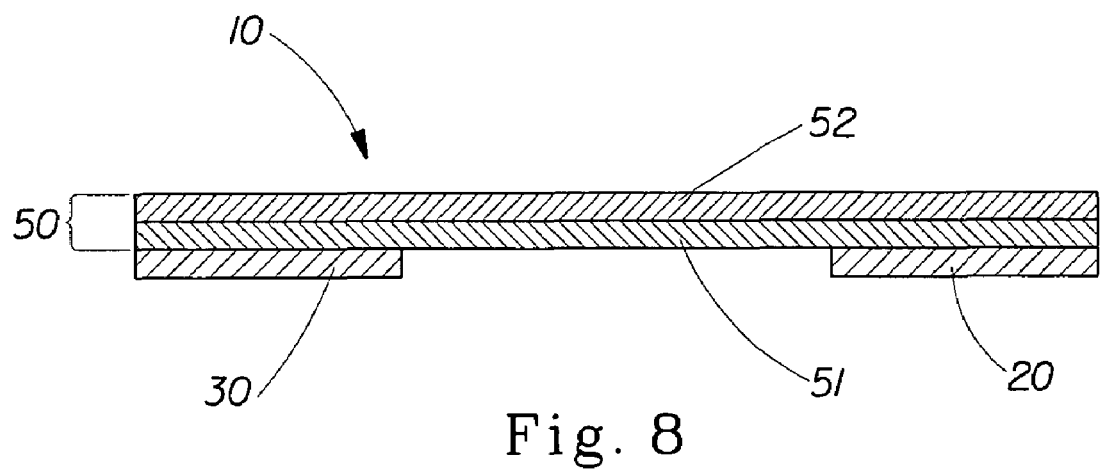
FIG. 8 is a section view of an exemplary absorbent core similar to that shown in FIG. 6, taken along line 8-8, with the portion of the core that faces the wearer oriented upward.

In the exemplary embodiment shown in cross section in FIG. 8 and corresponding to the general top view of FIG. 6, one upper absorbent layer 52 and one lower absorbent layer 51 are both placed over front and back panels 20 and 30, resulting in a thin, flexible absorbent core. The term "over" refers to the surface of the absorbent core of the invention corresponding to the wearer's body when used in an absorbent article such as a disposable diaper, i.e., the body-facing surface. It is noted, however, that FIG. 8 is representative of only one exemplary embodiment and it may be beneficial to place the absorbent layers 51 or 52 under the front and back panels 20 and 30. The term "under" refers to the surface of the absorbent core of the invention corresponding to the garment side when used in an absorbent article such as a catamenial pad or disposable diaper, i.e., the garment-facing surface. It should also be understood that the term "upper" refers to the absorbent layer of the absorbent core which is nearest to and faces the article topsheet; conversely, the term "lower" refers to the absorbent layer of the absorbent core which is nearest to and faces the article backsheet.

Figure 9:
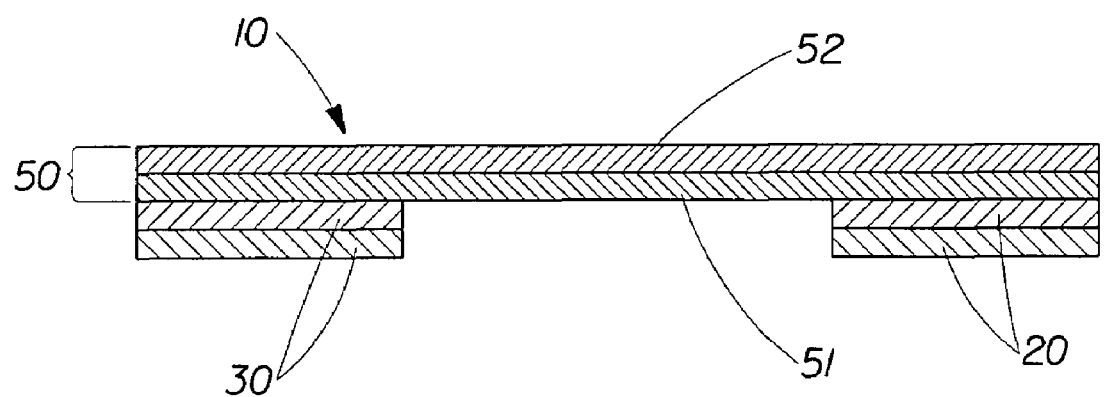
FIG. 9 shows a section view of another alternative exemplary absorbent core, with the portion of the core that faces the wearer oriented upward.
Figure 10:
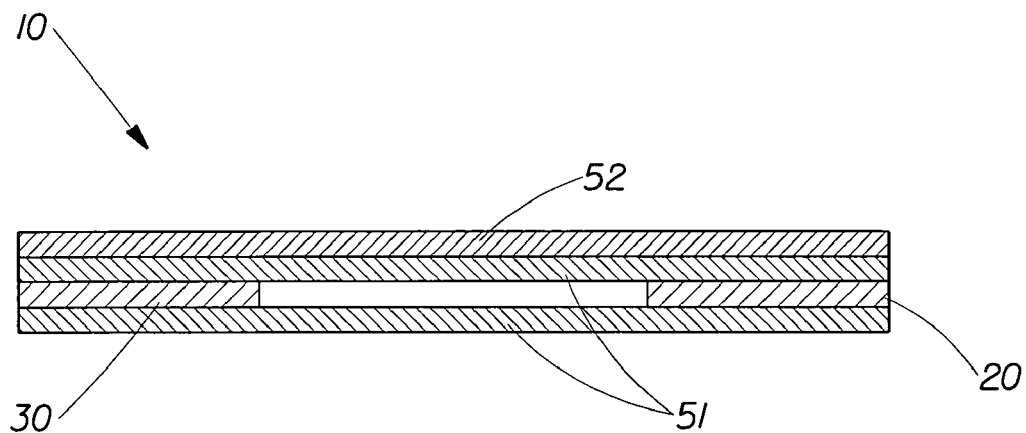
FIG. 10 shows a section view of another alternative exemplary absorbent core, with the portion of the core that faces the wearer oriented upward.
Figure 11:
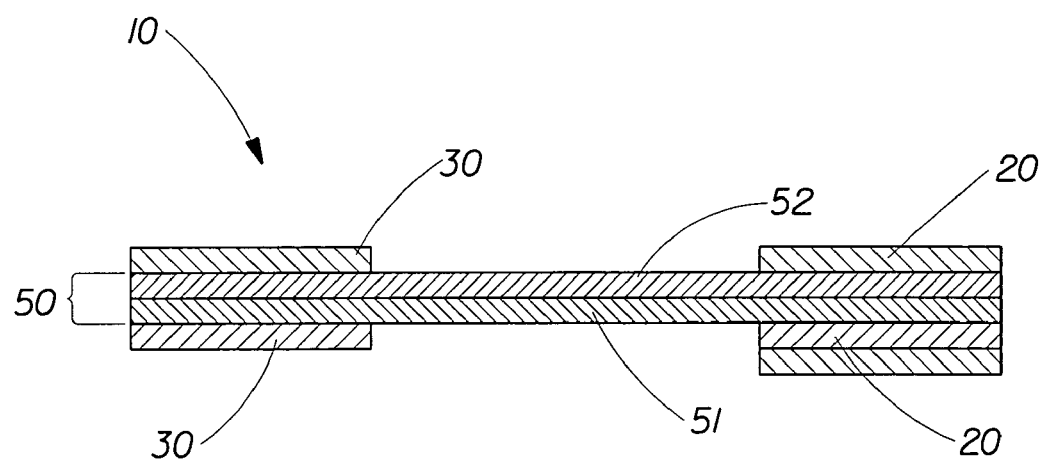
FIG. 11 shows a section view of another alternative exemplary absorbent core, with the portion of the core that faces the wearer oriented upward.

Other arrangements of the absorbent layers of the center section and the front and back panels are also possible. For example, FIG. 9 shows in cross-section an additional exemplary embodiment corresponding to the general top view of FIG. 6, in which two absorbent layers of front and back panels 20 and 30 are placed under the center section 50. As shown in the Weber et al. '602 patent and in FIG. 10, an alternative embodiment may have a center section 50 having two absorbent layers 51, one placed over front and back panels 20 and 30, and one placed under the front and back panels, thereby sandwiching the front and back panels between absorbent layers of the center section. As another example, as shown in the Weber et al. '602 patent and in FIG. 11, the front and back panels 20 and 30 may have two absorbent layers, with one absorbent layer placed over the center section 50 and one absorbent layer placed under the center section 50, thereby sandwiching the ends of the center section between absorbent layers of the front and back panels.

As shown in FIG. 8, the uppermost absorbent layer 52 is generally on the side corresponding to the body side of an absorbent article, such as a disposable diaper. Therefore, the uppermost absorbent layer 52 is generally in capillary liquid communication with the topsheet 61 of the disposable diaper, thereby acting to quickly acquire and partition bodily exudates away from the wearer's body to the generally more absorptive lower absorbent layers 51 and to the front and back panels 20 and 30. Adhesive bonding of the uppermost absorbent layer 52 to the topsheet 61 may enhance the capillary liquid communication by providing interfacial bonding and preventing topsheet separation from impeding liquid flow.

The Absorbent Core Materials

The components or members of the absorbent core may include laminates or combinations of several sheets or webs of the requisite types of materials. In general, each absorbent core component or member may be made of any absorbent material or combination of materials having enough structural integrity to be handled as a discrete unit.

Typical materials known in the art may be used for the absorbent core components and/or members, such as fibrous nonwoven materials, fibrous air-laid materials, fibrous wet-laid web materials, and combinations of fibrous materials having absorbent gelling materials dispersed upon or within the fibrous structure. If necessary, such absorbent core components or members may be formed into a packet having the fibrous materials substantially enveloped by a liquid pervious web that provides the structural integrity for the removal and replacement into the absorbent article. An exemplary form of a non-woven fibrous absorbent structure that may be utilized in the present invention is constructed from hydrophilic chemically stiffened cellulosic fibers, as taught in the Lash '728 patent and the Young et al. '345 patent, as well as in the Seger et al. '416 patent.

Absorbent materials for use as absorbent core components or members may also be foam-based. For example, a component of the absorbent core may include a foam material in the form of a sheet or a plurality of foam pieces or particles, which may be adhesively bonded together or which may simply be constrained into an unbonded aggregate held together by an overwrapping of envelope tissue or by means of the topsheet and backsheet of the absorbent article. Particularly suitable absorbent foams for absorbent articles such as diapers have been made from High Internal Phase Emulsions, hereafter referred to as "HIPE". See, for example, the DesMarais et al. '345 patent, the DesMarais et al. '224 patent, and the Stone et al. '179 patent.

The absorbent core of the absorbent articles described herein can also include a combination of conventional elements or materials and one or more foam absorbent structures. For example, the absorbent articles may utilize an absorbent core which includes a combination, e.g., an airlaid mixture, of particles or pieces of the foam absorbent structures and conventional absorbent materials such as wood pulp or other cellulosic fibers and/or particles or fibers of polymeric gelling agents.

Besides acquiring bodily liquids rapidly, the absorbent acquisition member of the present invention should give up this liquid efficiently to the liquid acquisition/distribution or storage/redistribution members. This liquid transfer function of the acquisition member is of particular importance because the acquisition member must have sufficient capillary suction to substantially drain the liquid from the topsheet and yet not exhibit excessive liquid retention, which would make it difficult for the underlying absorbent layer to desorb the acquisition member.

In particular, the liquid acquisition member should have a suitable capillary desorption pressure relative to the absorption pressure of other absorbent core members, especially those intended for liquid storage. If the liquid acquisition member of the absorbent article holds the acquired liquid too tenaciously, this will inhibit the ability of these other members to partition liquid away and can cause the acquisition member to remain so heavily loaded with liquid that the absorbent article is more susceptible to leaking.

The liquid acquisition/distribution member may include materials similar to those used in the acquisition member, but preferably having more distributive characteristics. Since discharged aqueous bodily liquid, e.g., urine, is frequently discharged in gushes, the acquisition/distribution member must be able to quickly acquire this liquid and must also transport the liquid by wicking or another mechanism from the point of initial liquid loading to other parts of the acquisition/distribution member for eventual desorption to the adjacent liquid storage/redistribution member. Thus, such materials preferably have a greater degree of distributive capacity than the acquisition member materials, such that bodily exudates may be efficiently transported from the acquisition zone to the storage members of the absorbent core.

In some embodiments, it may be desirable to have a "biased" absorbent core structure, wherein a portion adjacent to one surface is capable of rapidly acquiring a liquid with minimal dispersion, while a portion adjacent to an opposing surface is capable of rapidly dispersing a liquid with lesser acquisition capability. When oriented in an absorbent article such that the "acquisition side" is oriented toward the wearer and the "distribution side" is oriented away from the wearer, a "down and out" functionality is provided, whereby liquid is rapidly acquired into the absorbent core structure with minimal dispersion on its wearer-facing side and is rapidly distributed throughout the portion of the absorbent core structure on its garment-facing side. This functionality allows the maintenance of a clean and dry visible and tactile impression of the absorbent core structure, and hence the absorbent article, while effectively utilizing the absorptive capacity of the regions of the absorbent article oriented away from the wearer.

In order to provide the above-described functionality in some exemplary embodiments, compositions for the absorbent core may be selected such that the acquisition side of the absorbent layer is comparatively free of small, high surface area fibers which provide good distributive and storage characteristics but less than optimal acquisition characteristics and such that the distributive side of the absorbent layer has a comparatively higher proportion of such small, high surface area fibers so as to provide greater distribution characteristics. In some embodiments, the acquisition area may have both a relatively lower average density and lower average basis weight per unit area than the distribution area to establish the preferred capillarity force gradient between them. Also, in foam absorbent core structures, cell sizes and hole sizes are parameters that can impact a number of important mechanical and performance features of the foams, including their fluid wicking properties and the capillary pressure that is developed within the foam structure, as described in the Stone '179 patent.

Optionally, a liquid pervious sheet, e.g., a tissue sheet, or a scrim layer is positioned between the acquisition/distribution member and the storage/redistribution member to maintain the physical integrity of the acquisition/distribution member during processing and/or use. This liquid pervious sheet can envelop all or part of the acquisition/distribution member, or simply be positioned as described above, without necessarily enveloping the acquisition/distribution member. In embodiments in which the center section of the absorbent core includes the acquisition and acquisition/distribution members and is placed over or under a replaceable absorbent core component or absorbent insert including the storage/redistribution member, such as a back panel, a single such liquid pervious sheet may suffice. Alternatively, in embodiments in which absorbent layers of the center section sandwich the replaceable absorbent core component or absorbent insert, two or more such liquid pervious sheets may be positioned to separate the absorbent layers of the center section and the replaceable core component. These multiple liquid pervious sheets may be described as forming a surface of or lining the openable chassis pocket formed by and between the sandwiching absorbent layers of the center section. Similarly, in embodiments in which absorbent layers of a replaceable absorbent core component or absorbent insert sandwich an end of the center section, two or more such liquid pervious sheets may be positioned to separate the absorbent layers of the center section and the replaceable core component. In the latter embodiment, the multiple liquid pervious sheets may be described as forming a surface of or lining the two-part openable chassis pocket into which the replaceable absorbent core component or absorbent insert is inserted and which is formed by and between the topsheet and the center section and by and between the center section and the backsheet, respectively.

An absorbent core suitable for use with the present invention includes at least one absorbent core component including a liquid storage/redistribution member and may include two such components, e.g., in the form of front and back panels. Each absorbent core component having a liquid storage/redistribution member acts to store bodily exudates away from the wearer's body, so as to leave the wearer with a feeling of dryness and to prevent leakage. The absorbent core component having the liquid storage/redistribution member is maintained in capillary liquid communication with the acquisition and/or acquisition/distribution member(s), such that urine or other aqueous bodily liquid can be desorbed from the acquisition and/or acquisition/distribution member(s) and be absorbed by the liquid storage/redistribution member.

The storage/redistribution member may include a member or members having primarily liquid storage characteristics. Such a storage member may have limited transport and wicking capabilities but high storage or retention capacity, and rely upon a liquid distribution member to distribute incoming liquid over a larger area of the storage/redistribution member.

An exemplary material capable of providing absorption pressures suitable for use in a storage/redistribution member is a collapsed polymeric foam material comprising a hydrophilic, flexible, nonionic polymeric foam structure of interconnected open cells, which foam material, upon contact with body temperature liquid, expands and absorbs the liquid. An important parameter of these foams is their glass transition temperature. The glass transition temperature represents the midpoint of the transition between the glassy and rubbery states of the polymer. Foams that have a higher glass transition temperature than the temperature of use can be very strong but will also be very rigid and potentially prone to fracture. When such foams are collapsible, but have been stored in the collapsed state for prolonged periods, they also typically take a long time to recover to the expanded state when wetted with aqueous fluids colder than the glass transition temperature of the polymer. Such a foam may have a capillary suction specific surface area per gram in the range from about 0.7 to about 8 $m^2/g$ or, preferably, from about 1 to about 7 $m^2/g$, and most preferably from about 1.5 to about 6 $m^2/g$. Such a foam will preferably have a number average cell size of about 50 microns or less and typically in the range of from about 5 to about 50 microns. More preferably, the number average cell size will be in the range from about 5 to about 40 microns and, most preferably, from about 5 to about 35 microns.

In summary, the absorbent core 10 includes a plurality of discrete components, each component having distinct liquid acquisition, acquisition/distribution, or storage/redistribution characteristics. So long as each of the acquisition, acquisition/distribution, and storage/redistribution members is in capillary liquid communication with an adjacent member or members, the absorbent core components may be positioned relative to one another in a wide variety of configurations. There is no particular criticality with respect to the positional relationship of the acquisition/distribution member and the liquid storage/redistribution member within the absorbent core so long as these members are in effective capillary liquid communication with each other and so long as each member is capable of effectively holding and/or transporting the amount of aqueous bodily liquid that is expected to be discharged into the absorbent article. It should be noted that the various structures of absorbent articles according to the present invention may or may not be generally planar in nature, and may be shaped or profiled in any desired configuration.

The Structure Allowing Removal and Replacement of Core Components

As shown in FIG. 2, FIG. 3, and FIG. 4, the backsheet 62 of some exemplary embodiments of an absorbent article of the present invention may have an aperture 44 in the general proximity of the front panel 20 or rear panel 30, or both.

As shown in FIG. 4, the aperture 44 provides access into what may be described as an openable chassis pocket 5, with a removable absorbent core component, for example, the back panel 30, being disposed inside the openable chassis pocket when the diaper is being worn, and being removable from and replaceable into the openable chassis pocket through the aperture. For example, after the removal of a saturated back panel, a fresh, unused absorbent core component may be reinserted through the aperture. A flap 42 may be provided to cover the aperture. The material used for the backsheet may be used for the flap as well. When the disposable diaper is being worn, the flap may be secured over the aperture by suitable fasteners 43, such as VELCRO strips or adhesive strips (not shown). For example, FIG. 4 shows the flap in the closed position over the aperture adjacent to the front panel 20 (shown in FIG. 3). More preferably, the flap is sealed with releasable adhesive, thereby providing for liquid impermeability when closed, but allowing for multiple openings and closings.

In the exemplary embodiment shown in FIG. 3 and FIG. 4, the back panel 30 is disposed under the center section, as in the description of FIG. 8, above, and the openable chassis pocket 5 is formed by and between the center section 50 and the backsheet 62. In other exemplary embodiments, in which the center section and the removable core component or components are arranged differently, the openable chassis pocket may be formed by and between different components and layers. For example, in an embodiment in which the back panel is disposed above the center section, the openable chassis pocket may be formed by and between a topsheet and the center section. Similarly, when the back panel is sandwiched between absorbent layers of the center section, as in FIG. 10, the openable chassis pocket may be formed by and between the sandwiching absorbent layers of the center section. Also, when the center section is sandwiched between absorbent layers of the back panel, as in FIG. 11, the openable chassis pocket may be formed in two parts, by and between the topsheet and the center section and by and between the center section and the backsheet, respectively.

In general, the front panel, the back panel, and the corresponding apertures and flaps are substantially similar, but need not be. In an alternative exemplary embodiment, it may be desired to include only one aperture and flap, for example, for access to the back panel, without providing a similar aperture for access to the front panel.

Figure 12:
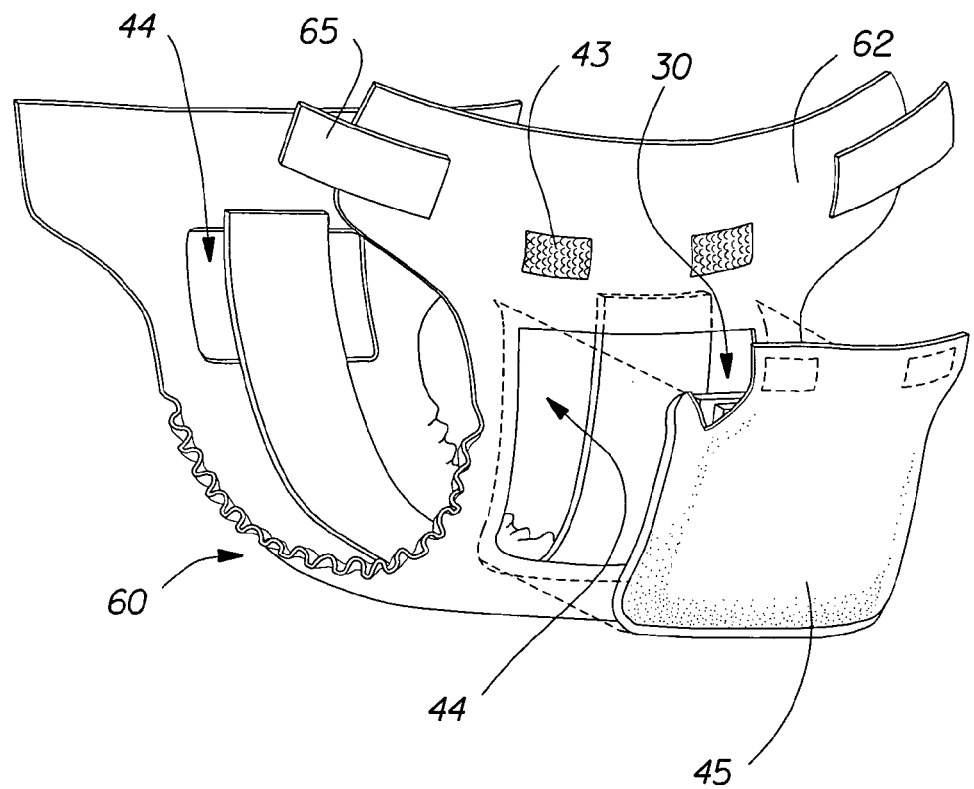
FIG. 12 is an exploded, perspective, partially segmented illustration of an alternative exemplary absorbent article according to the present invention.

Alternatively, as shown in FIG. 12 and FIG. 13, a backsheet pocket sheet 45 may be affixed on the garment-facing surface of the backsheet adjacent to the aperture 44 to form an openable chassis pocket 5 between the backsheet pocket sheet and the backsheet. In these embodiments, a removable and replaceable core component, such as back panel 30, may be disposed outside, relative to the aperture, and a core component that remains in the absorbent article, i.e., a non-removable core component, such as center section 50, may be disposed inside, relative to the aperture, such that the aperture allows capillary liquid communication between the replaceable core component and the non-removable core component.

The openable chassis pocket 5 formed by the backsheet pocket sheet 45 may have its openable end 41 longitudinally nearest the adjacent waist end edge. The openable chassis pocket may be reclosable and may be resealable, and is preferably positioned so that the back panel is urged into capillary liquid communication with the center section. The backsheet pocket sheet is preferably resilient and pliable, and forms a substantially liquid impervious barrier over the aperture, functionally becoming an extension of the backsheet when the openable chassis pocket is closed.

The back panel is shown in FIG. 13 as a core component made up of individual back panel absorbent layers 34, 35, and 36. In such an embodiment, as one back panel absorbent layer, e.g., the uppermost back panel absorbent layer 34, becomes saturated with bodily discharge it may be removed, thereby exposing an adjacent propositioned back panel absorbent layer, e.g., the adjacent back panel absorbent layer 35.

Figure 14:
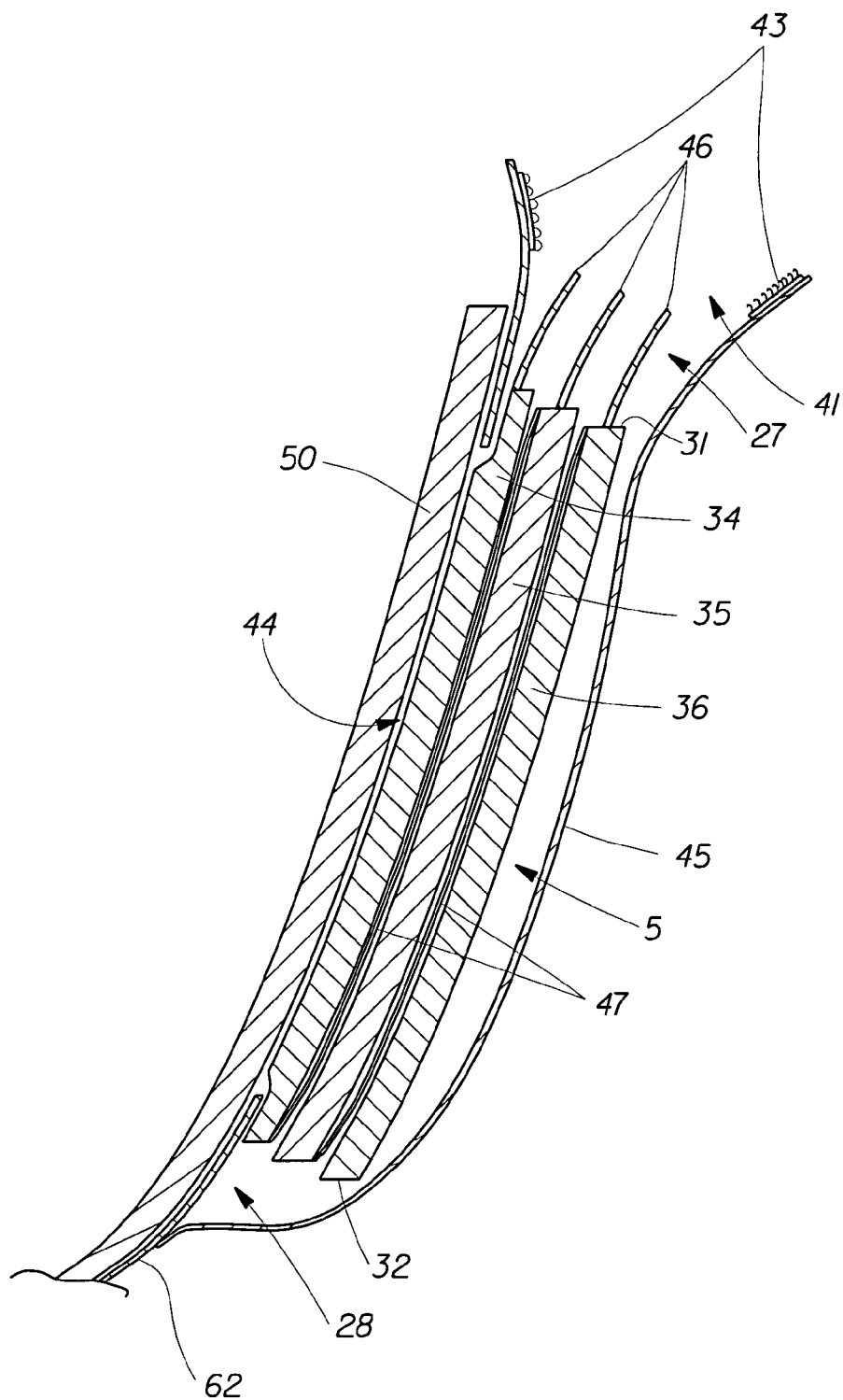
FIG. 14 is a cross-section illustration of a portion of an exemplary absorbent article having an opening through the backsheet.

FIG. 14 shows an exemplary embodiment of the arrangement of the back panel 30, again showing representative back panel absorbent layers 34, 35, and 36 in a layered relationship adjacent to the aperture 44 and in capillary liquid communication with the center section 50. Removal of the back panel absorbent layers through the openable end 41 of the openable chassis pocket 5 may be facilitated by the use of pull tabs 46, which may be of any type known in the art, such as a strip of plastic film adhered to each back panel absorbent layer.

Additionally, the back panel absorbent layers may be separated from one another by a liquid impervious blocking layer 47 so that adjacent back panel absorbent layers are not in capillary liquid communication with each other. The blocking layer 47 may be any liquid impervious polymer film, such as film suitable for use as a liquid impervious backsheet. As one back panel absorbent layer becomes saturated by absorption of liquid from the center section 50, it may be removed, thereby exposing a substantially dry, fresh adjacent back panel absorbent layer for additional absorption from the center section 50. In this manner, the absorbent article may be refreshed or regenerated for a prolonged period of time without the necessity of its removal from the wearer.

Figure 15:
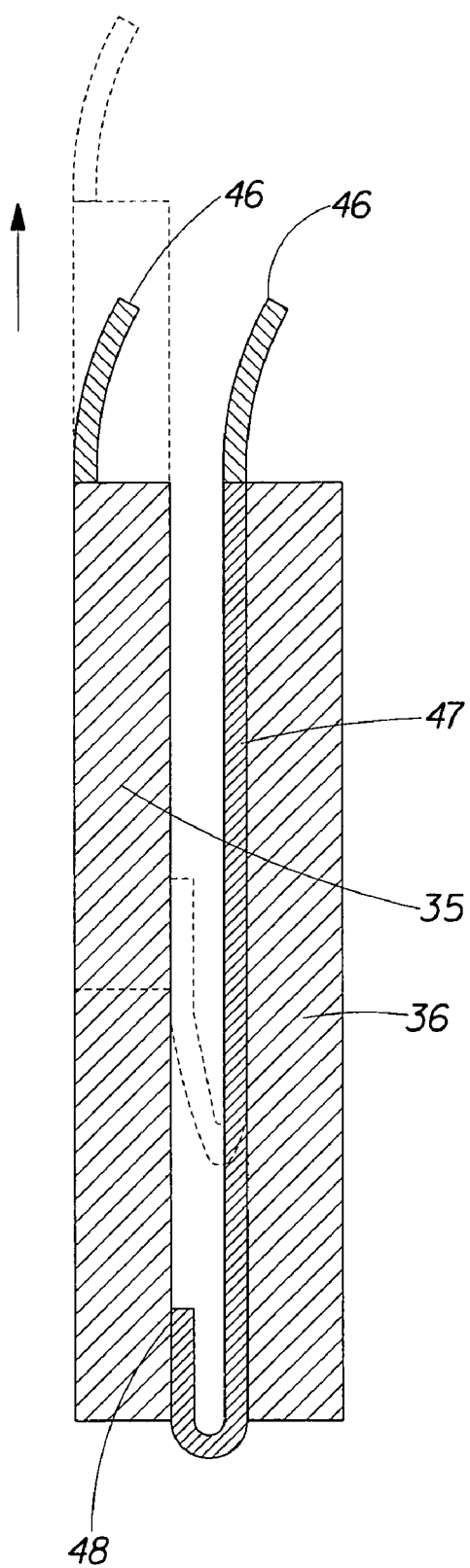
FIG. 15 is a cross-section detail of an exemplary configuration of removable and replaceable absorbent core layers.

FIG. 15 shows an exemplary arrangement of the back panel absorbent layers 35 and 36 in a layered relationship with the liquid impervious blocking layer 47 disposed to form a liquid impervious layer between them. A portion of the blocking layer is preferably affixed, for example at an attachment point 48, to the back panel absorbent layer being removed. As this back panel absorbent layer 35 is removed, the blocking layer 47 is removed as well, thereby leaving the adjacent back panel absorbent layer 36 in position to be urged into capillary liquid communication with the center section 50.

Figure 16:
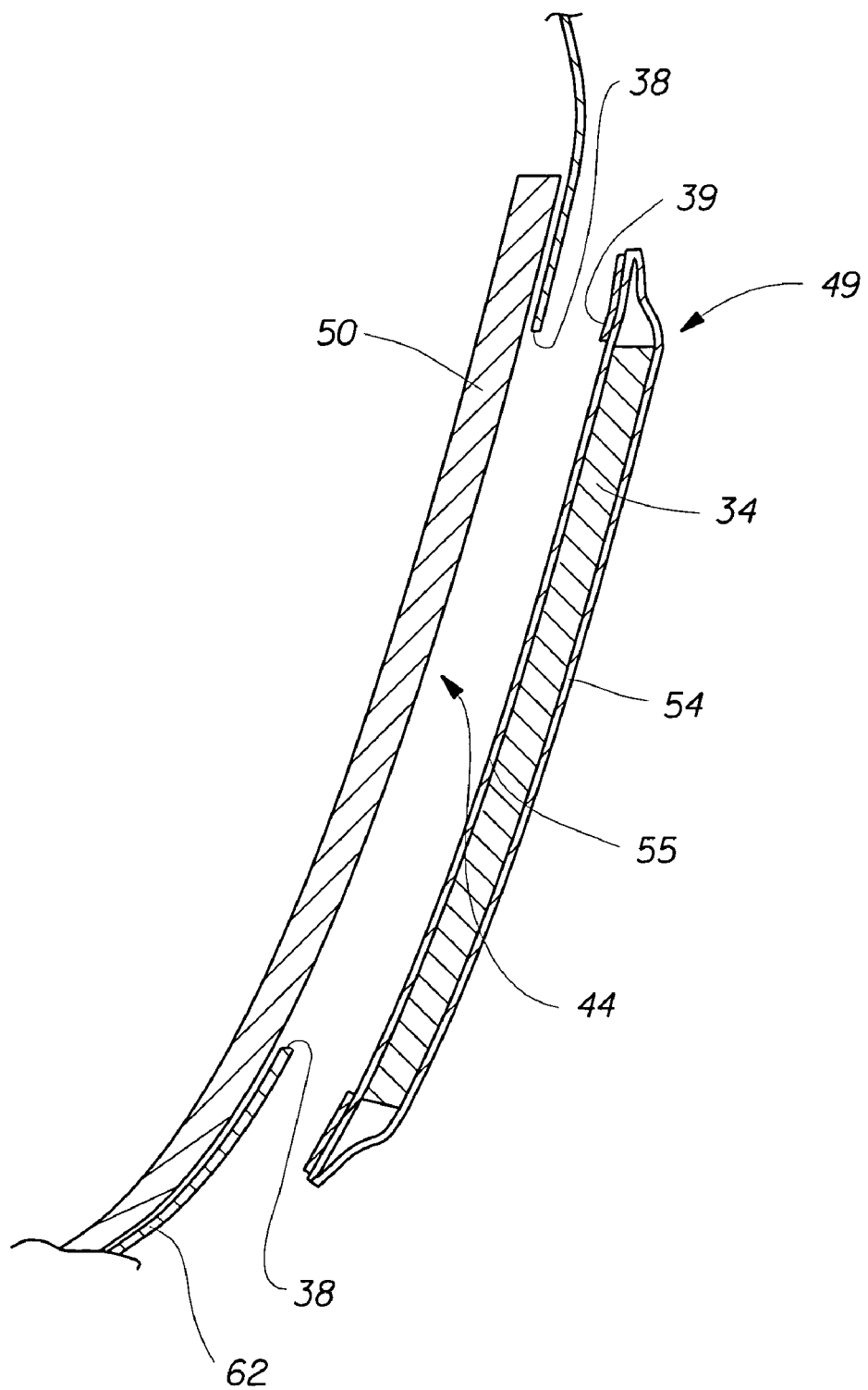
FIG. 16 is a cross-section detail of an alternative exemplary configuration of a removable and replaceable absorbent core component.

An alternative exemplary embodiment of the back panel 30 of an absorbent article of the present invention is shown in cross-section in FIG. 16, in which a back panel envelope 49 is shown in position to be attached to the backsheet 62. The back panel envelope is shown as containing a single back panel absorbent layer 34 enveloped between a substantially liquid impervious layer 54 and a substantially liquid pervious layer 55, and may be releasably affixed, for example, by a suitable releasable adhesive 39 known in the art, adjacent to the perimeter 38 of the aperture 44. When such a releasably affixed back panel envelope becomes saturated due to the absorption of liquid from the center section 50, it may be removed and replaced with a fresh, dry back panel envelope 49.

Figure 17:
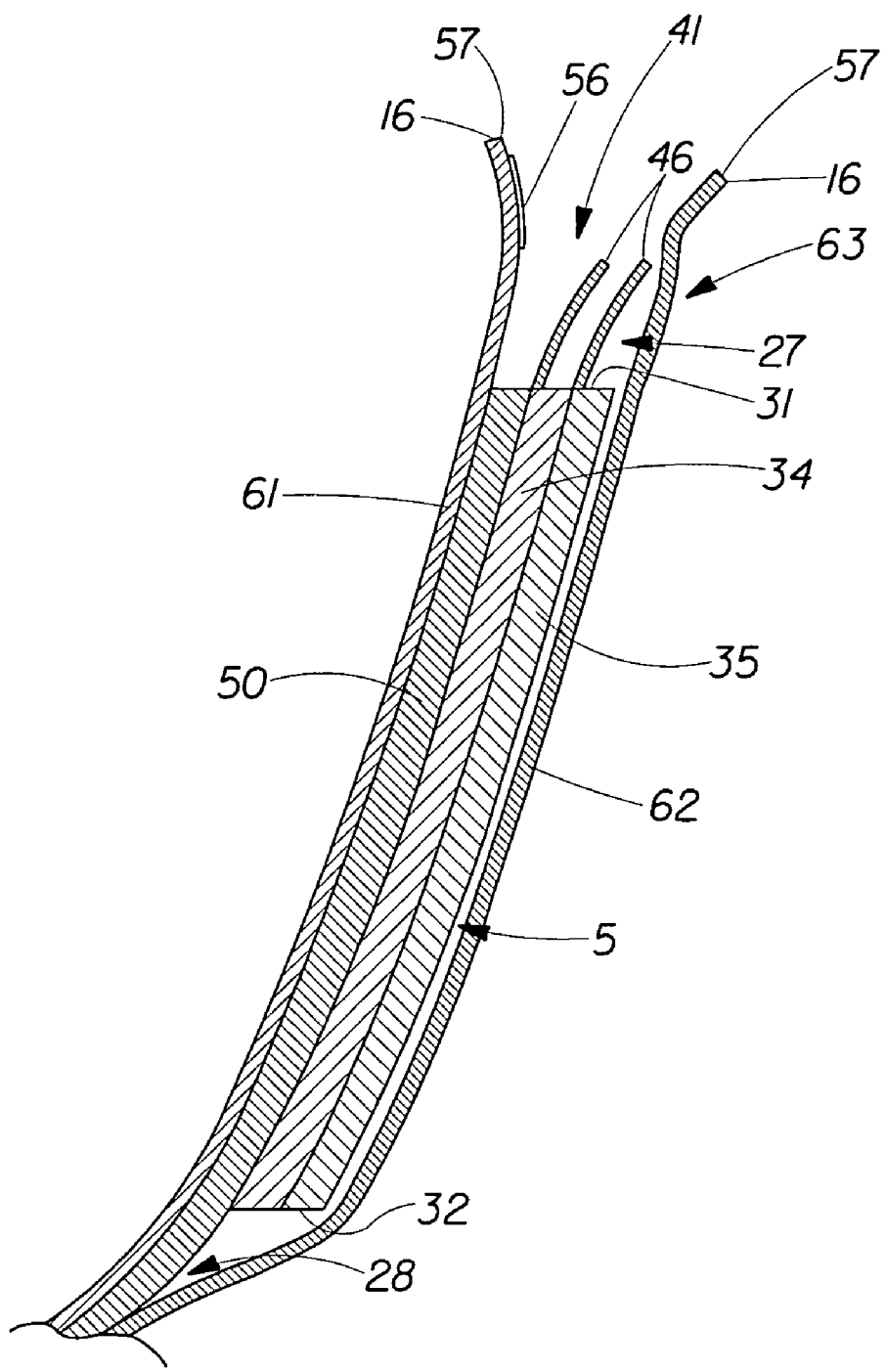
FIG. 17 is a cross-section depiction of an additional alternative exemplary configuration of removable and replaceable absorbent core layers.

In another alternative exemplary embodiment of an absorbent article of the present invention shown in cross-section in FIG. 17, the openable end 41 of the openable chassis pocket 5 may be formed along a predetermined area of the periphery 57, such as along the waist end edge 16, either in the front, in the back, or both, where the topsheet 61 and the backsheet 62 are separable to provide access to the removable absorbent core component, e.g., the back panel absorbent layers 34 and 35. The openable end formed by the separation of the topsheet and the backsheet allows the removal and replacement of the removable absorbent core components and may be resealable to provide a substantial degree of liquid impermeability when closed. The openable end may be made resealable, for example, with a suitable releasable and resealable adhesive 56 known in the art.

As can be seen in FIG. 14 and in FIG. 17, the openable chassis pocket 5 generally has an outer end 27 and an inner end 28 corresponding to the outer end 31 and the inner end 32, respectively, of the back panel 30. In the exemplary embodiments shown in FIG. 14 and FIG. 17, the outer end 27 of the openable chassis pocket coincides with its openable end 41. The inner end of the openable chassis pocket may be formed in several ways. For example, as shown in FIG. 14, the inner end may be formed at the area of attachment of the backsheet pocket sheet 45 to the backsheet. As described above, the backsheet, the topsheet, and the non-removable absorbent core component may be secured, attached, or affixed to each other in a variety of configurations. Thus, as another example of the formation of the inner end of the openable chassis pocket, an area of attachment of the non-removable absorbent core component to the chassis, e.g., to the backsheet, the topsheet, or both, in the crotch region may form the inner end of the openable chassis pocket.

As described in the chassis description, an elastic waistband 67 may be disposed in the waistband region 63 between the waist end edge 16 and the adjacent end of the absorbent core, as shown in FIG. 1 and in FIG. 2. When such an elastic waistband is disposed adjacent to an opening formed by the separation of the topsheet and the backsheet along a waist end edge, the waistband may serve to make the opening elastically openable and self-closing. For example, such an elastic waistband, formed as either a separate element affixed to the backsheet or as an extension of the backsheet in the waistband region, may exert a contractive force tending to draw the waist end edge of the backsheet at the periphery toward the topsheet, thus tending to close the openable end of the openable chassis pocket when it is released.

As another example, an elastic waistband, formed as either a separate element affixed to the topsheet or as an extension of the topsheet in the waistband region, may exert a contractive force tending to hold the waist end edge of the topsheet against the body of the wearer at all times, including when the waist end edge of the backsheet is pulled away from the topsheet to form the opening and thereby gain access into the openable chassis pocket. In addition, as described above in the chassis description, a flexible substrate forming the chassis, such as the backsheet and the topsheet, may be elasticized or otherwise extensible. Thus, the superposed or layered portions of both the topsheet and the backsheet in the openable area along the waist end edge may be elastically contractible, either by means of a waistband or otherwise. In such an embodiment, when the backsheet is pulled away for access into the openable chassis pocket, the waist end edge of the topsheet may be held elastically against the body of the wearer, thereby facilitating the access, and the opening may also be self-closing by means of the elastic contraction of the waist end edge of the backsheet when it is released.

Figure 18:
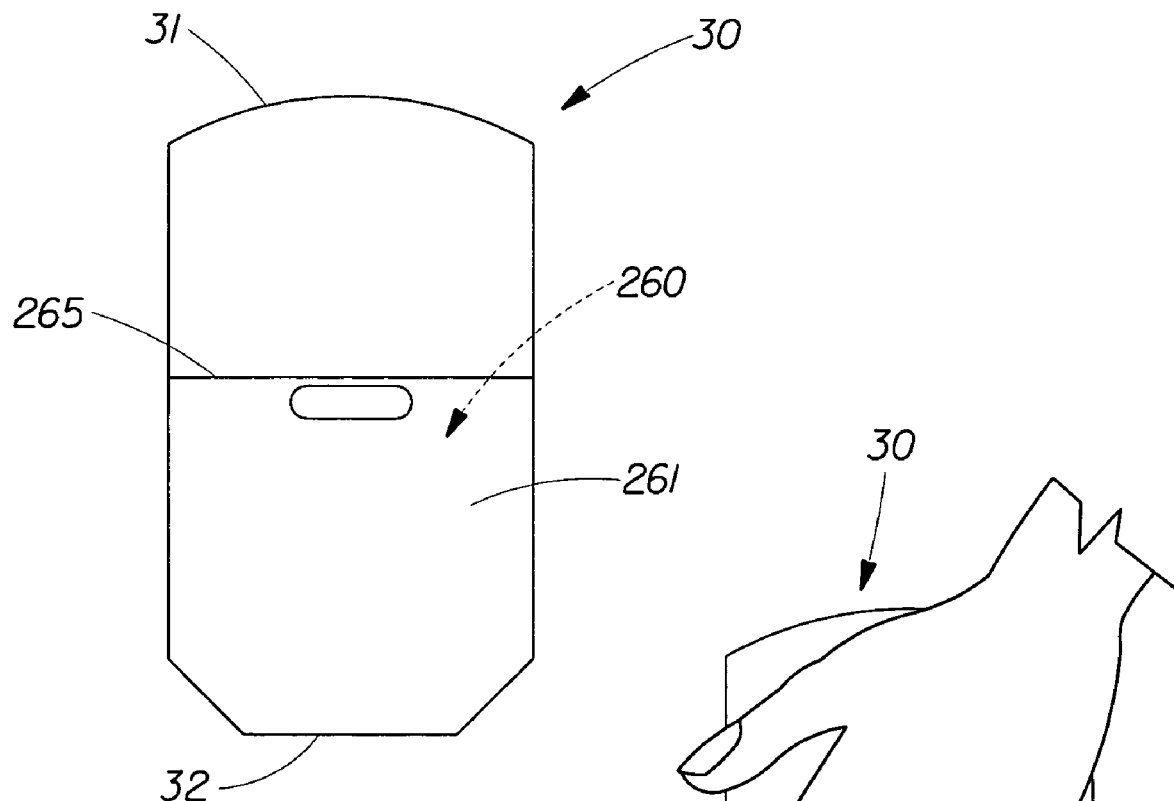
FIG. 18 is a plan view of an exemplary replaceable absorbent core component showing an openable insertion pocket disposed on its major surface.
Figure 19:
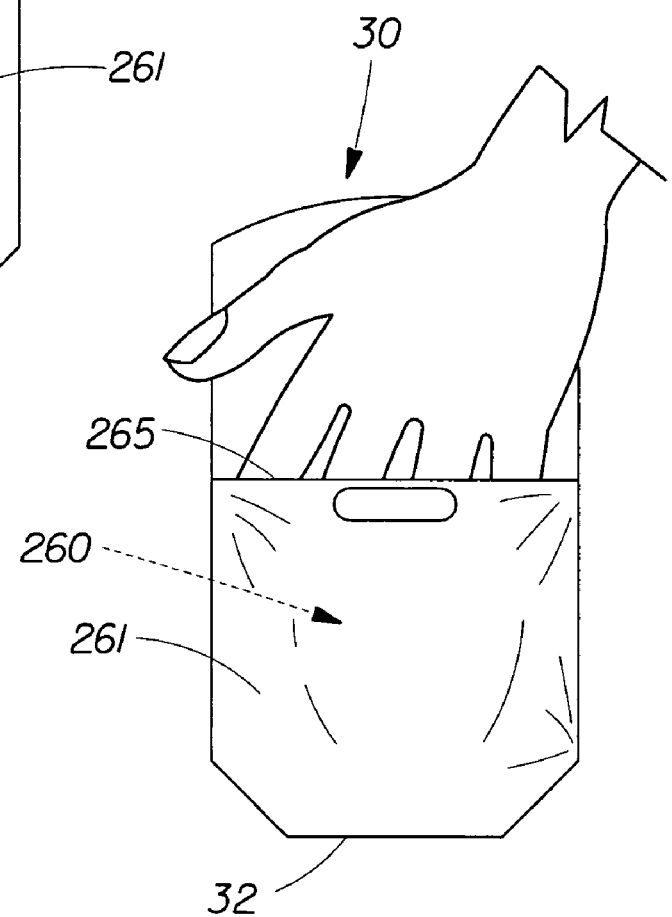
FIG. 19 is a plan view of the exemplary replaceable absorbent core component of FIG. 18 showing the fingers of a user's hand partially inserted into the openable end of the openable insertion pocket.

The replaceable core component may include an openable insertion pocket 260 into which a finger or fingers may be inserted for the application of a force to insert the replaceable core component into the chassis in the intended predetermined orientation. Such an insertion pocket may be formed by the attachment of an insertion pocket sheet 261 onto a major surface of the replaceable core component, e.g., the back panel 30, in a configuration such as that shown in FIG. 18 and FIG. 19. In this embodiment, the insertion pocket has its openable end 265 facing away from the inner end 32 of the back panel.

The insertion pocket may be designed such that the user can slip his or her fingers or hand into the insertion pocket with the replaceable core component either lying in the palm of the hand or positioned on the outside of the fingers. In other words, the hand can be inserted into the insertion pocket with the palm side toward the replaceable absorbent core component or with the palm side of the hand away from the replaceable absorbent core component. Thus, the user can select an orientation of the hand relative to the replaceable core component corresponding to his or her bodily position relative to the wearer. For example, if standing behind the wearer, the user may choose one orientation while, if standing in front of the wearer and reaching over or around to insert a back panel, the user may choose an alternative orientation.

The insertion pocket sheet may comprise a fibrous nonwoven material, either hydrophobic or hydrophilic, a substantially liquid impermeable film material, an elastomeric film material, or combinations thereof, and may thereby be liquid impervious or liquid pervious. In some embodiment, the insertion pocket sheet may comprise an elastomeric material forming the overall pocket or forming an additional component attached to the aforementioned materials. The insertion pocket sheet may be highly extensible such that it can be extended and then wrapped over the replaceable core component once it is removed and folded, thus allowing for clean and easy disposal of the used replaceable core component. The insertion pocket sheet may be detachable along the side portions of the replaceable core component such that it forms a flap that can be wrapped around the end of the replaceable core component in order to cover the liquid transfer region for sanitary handling and disposal.

Incorporation by Reference

The disclosures of all patents, patent applications, and any patents which issue thereon, as well as any corresponding published foreign patent applications, and all publications listed and/or referenced in this description, are hereby incorporated herein by reference. It is expressly not admitted, however, that any of the documents or any combination of the documents incorporated herein by reference teaches or discloses the present invention.

LIST OF U.S. PATENT REFERENCES

U.S. Pat. No. 3,848,594 to Buell, issued Nov. 19, 1974
U.S. Pat. No. 3,860,003 to Buell, issued Jan. 14, 1975
U.S. Pat. No. 4,062,817 to Westerman, issued Dec. 13, 1977
U.S. Pat. No. 4,076,663 to Masuda et al., issued Feb. 28, 1978
U.S. Pat. No. 4,081,301 to Buell, issued Mar. 28, 1978
U.S. Pat. No. 4,260,443 to Lindsay et al., issued Apr. 7, 1981
U.S. Pat. No. 4,467,012 to Pedersen et al., issued Aug. 21, 1984
U.S. Pat. No. 4,515,595 to Kievit et al., issued May 7, 1985
U.S. Pat. No. 4,625,001 to Tsubakimoto et al., issued Nov. 25, 1986
U.S. Pat. No. 4,654,039 to Brandt et al., issued Mar. 31, 1987 (reissued Apr. 19, 1988 as U.S. Pat. No. Re. 32,649)
U.S. Pat. No. 4,666,983 to Tsubakimoto et al., issued May 19, 1987
U.S. Pat. No. 4,695,278 to Lawson, issued Sep. 22, 1987
U.S. Pat. No. 4,715,918 to Lang, issued Dec. 29, 1987
U.S. Pat. No. 4,773,903 to Weisman et al., issued Sep. 27, 1988
U.S. Pat. No. 4,808,178 to Aziz et al., issued Feb. 28, 1989
U.S. Pat. No. 4,816,025 to Foreman, issued Mar. 28, 1989
U.S. Pat. No. 4,822,453 to Dean et al., issued Apr. 18, 1989
U.S. Pat. No. 4,851,069 to Packard et al., issued Jul. 25, 1989
U.S. Pat. No. 4,888,093 to Dean et al., issued Dec. 19, 1989
U.S. Pat. No. 4,898,642 to Moore et al., issued Feb. 6, 1990
U.S. Pat. No. 4,923,454 to Seymour et al., issued May 8, 1990
U.S. Pat. No. 4,950,264 to Osborn, issued Aug. 21, 1990
U.S. Pat. No. 4,988,344 to Reising et al., issued Jan. 29, 1991
U.S. Pat. No. 4,988,345 to Reising, issued Jan. 29, 1991
U.S. Pat. No. 4,994,037 to Bernardin, issued Feb. 19, 1991
U.S. Pat. No. 5,009,650 to Bernardin, issued Apr. 23, 1991
U.S. Pat. No. 5,009,653 to Osborn, issued Apr. 23, 1991
U.S. Pat. No. 5,061,259 to Goldman et. al, issued Oct. 29, 1991
U.S. Pat. No. 5,102,597 to Roe et al., issued Apr. 7, 1992
U.S. Pat. No. 5,128,082 to Makoui, issued Jul. 7, 1992
U.S. Pat. No. 5,137,537 to Herron et al., issued Aug. 11, 1992
U.S. Pat. No. 5,147,345 to Young et al., issued Sep. 15, 1992
U.S. Pat. No. 5,149,335 to Kellenberger et al., issued Sep. 22, 1992
U.S. Pat. No. 5,176,668 to Bernardin, issued Jan. 5, 1993
U.S. Pat. No. 5,217,445 to Young et al., issued Jun. 8, 1993
U.S. Pat. No. 5,260,345 to DesMarais et al., issued Nov. 9, 1993
U.S. Pat. No. 5,268,224 to DesMarais et al., issued Dec. 7, 1993
U.S. Pat. No. 5,324,561 to Rezai et al., issued Jun. 28, 1994
U.S. Pat. No. 5,358,500 to LaVon et al., issued Oct. 25, 1994
U.S. Pat. No. 5,387,207 to Dyer et al., issued Feb. 7, 1995
U.S. Pat. No. 5,531,728 to Lash, issued Jul. 2, 1996
U.S. Pat. No. 5,549,589 to Horney et al., issued Aug. 27, 1996
U.S. Pat. No. 5,550,167 to Des Marais et al., issued Aug. 27, 1996
U.S. Pat. No. 5,562,646 to Goldman et al., issued Oct. 8, 1996
U.S. Pat. No. 5,563,179 to Stone et al., issued Oct. 18, 1996
U.S. Pat. No. 5,599,335 to Goldman et al., issued Feb. 4, 1997
U.S. Pat. No. 5,650,222 to DesMarais et al., issued Jul. 22, 1997
U.S. Pat. No. 5,800,416 to Seger et al., issued Sep. 1, 1998
U.S. Pat. No. 5,843,055 to Seger et al., issued Dec. 1, 1998
U.S. Pat. No. 5,906,602 to Weber et al., issued May 25, 1999

Those skilled in the art will recognize that additional exemplary embodiments of absorbent articles providing access to a removable and replaceable absorbent core component or absorbent insert are possible without departing from the scope of the present invention. Furthermore, it is contemplated that, without departing from the scope of the present invention, additional combinations of the absorbent core components, the absorbent core members, the placement of the absorbent core components and members, and the absorptive characteristics may be used, with the desired functional requirements influencing the ultimate design. Specifically, not only the illustrated embodiments, but all structurally feasible combinations of the disclosed elements and configurations are contemplated.

While particular exemplary embodiments of the present invention have been illustrated and described, it would be obvious to those skilled in the art that various other changes and modifications can be made without departing from the spirit and scope of the present invention. The foregoing is therefore intended to cover in the appended claims all such changes and modifications that are within the scope of the present invention.

What is claimed is:

1. A disposable absorbent article adapted to be worn about a lower torso of a human body, comprising:
   a chassis forming a waist opening and a pair of leg openings and having longitudinally opposing first and second waist end edges, longitudinally opposing first and second waist regions adjacent to the respective waist end edges, and a crotch region longitudinally intermediate of the waist regions;
   a non-removable absorbent core component disposed in the crotch region; and
   a replaceable absorbent core component disposed in capillary liquid communication with the non-removable absorbent core component and having a first major surface and an opposing second major surface, the replaceable absorbent core component further comprising an openable insertion pocket;
   wherein at least one of the first major surface and the second major surface has a liquid impermeable region and a liquid permeable region.

2. The disposable absorbent article of claim 1 wherein the replaceable absorbent core component has an inner end and the openable insertion pocket has an openable end facing away from the inner end.

3. The disposable absorbent article of claim 1 wherein the liquid impermeable region and the liquid permeable region are disposed on the second major surface.

4. The disposable absorbent article of claim 1 wherein the chassis comprises a wearer-facing layer and a garment-facing layer forming an openable chassis pocket adapted to receive the replaceable absorbent core component and the replaceable absorbent core component is removably disposed inside the openable chassis pocket.

5. The disposable absorbent article of claim 1 wherein the chassis comprises a wearer-facing layer and a garment-facing layer forming an openable chassis pocket adapted to receive the replaceable absorbent core component, the replaceable absorbent core component is removably disposed inside the openable chassis pocket, and the openable chassis pocket has an inner end located in the crotch region and formed by an area of joining of the wearer-facing layer and the non-removable absorbent core component, the garment-facing layer and the non-removable absorbent core component, the wearer-facing layer and the garment-facing layer and the non-removable absorbent core component, or the wearer-facing layer and the garment-facing layer.

6. The disposable absorbent article of claim 1 wherein the liquid impermeable region and the liquid permeable region are disposed on the first major surface.

7. An article of commerce comprising a disposable absorbent article adapted to be worn about a lower torso of a human body, the absorbent article comprising:
   a chassis forming a waist opening and a pair of leg openings and having longitudinally opposing first and second waist end edges, longitudinally opposing first and second waist regions adjacent to the respective waist end edges, and a crotch region longitudinally intermediate of the waist regions;
   a non-removable absorbent core component disposed in the crotch region; and
   a replaceable absorbent core component disposed in capillary liquid communication with the non-removable absorbent core component and having a first major surface and an opposing second major surface, the replaceable absorbent core component further comprising an openable insertion pocket;
   wherein at least one of the first major surface and the second major surface has a liquid impermeable region and a liquid permeable region,
   the article of commerce further comprising instructions for removing the replaceable absorbent core component from the absorbent article, inserting the replaceable absorbent core component into the absorbent article, inserting a like replacement of the replaceable absorbent core component into the absorbent article, or replacing the replaceable absorbent core component by removing the replaceable absorbent core component from the absorbent article and inserting a like replacement of the replaceable absorbent core component into the absorbent article.

8. The article of commerce of claim 7 wherein the instructions include instructions for using the insertion pocket to insert the replaceable absorbent core component into the absorbent article.

* * * * *

UNITED STATES PATENT AND TRADEMARK OFFICE
CERTIFICATE OF CORRECTION

PATENT NO. : 7,601,145 B2
APPLICATION NO. : 10/410783
DATED : October 13, 2009
INVENTOR(S) : LaVon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 491 days.

Signed and Sealed this

Fifth Day of October, 2010

David J. Kappos
*Director of the United States Patent and Trademark Office*